(12) United States Patent
Schulze zur Wiesche

(10) Patent No.: US 8,900,561 B2
(45) Date of Patent: *Dec. 2, 2014

(54) HAIR TREATMENT AGENTS CONTAINING 4-MORPHOLINO-METHYL-SUBSTITUTED SILICONE(S) AND CONDITIONING AGENT(S)

(71) Applicant: Henkel AG & Co. KGaA, Duesseldorf (DE)

(72) Inventor: Erik Schulze zur Wiesche, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/291,307

(22) Filed: May 30, 2014

(65) Prior Publication Data

US 2014/0271750 A1    Sep. 18, 2014

Related U.S. Application Data

(63) Continuation of application No. PCT/EP2012/072223, filed on Nov. 9, 2012.

(30) Foreign Application Priority Data

Dec. 2, 2011    (DE) .......................... 10 2011 087 624

(51) Int. Cl.
| | | |
|---|---|---|
| *A61Q 5/00* | (2006.01) | |
| *A61K 8/81* | (2006.01) | |
| *A61K 8/06* | (2006.01) | |
| *A61K 8/892* | (2006.01) | |
| *A61K 8/891* | (2006.01) | |
| *A61Q 5/12* | (2006.01) | |

(52) U.S. Cl.
CPC ............... *A61K 8/891* (2013.01); *A61K 8/8135* (2013.01); *A61K 8/062* (2013.01); *A61K 8/8188* (2013.01); *A61K 8/892* (2013.01); *A61Q 5/00* (2013.01); *A61Q 5/12* (2013.01)
USPC ...................................... 424/70.122; 424/489

(58) Field of Classification Search
CPC ............. A61Q 5/06; A61Q 5/12; A61Q 5/04; A61K 8/25; A61K 8/585; A61K 8/898
USPC ............................................ 424/70.122, 489
See application file for complete search history.

(56) References Cited

U.S. PATENT DOCUMENTS 6,824,764 B2 * 11/2004 Devin-Baudoin et al. ... 424/70.1

OTHER PUBLICATIONS

STIC Search Report dated Jun. 20, 2014.*

* cited by examiner

*Primary Examiner* — Eisa Elhilo
(74) *Attorney, Agent, or Firm* — David K. Benson

(57) ABSTRACT

Cosmetic compositions include in a cosmetically acceptable medium at least one thickening agent and at least one 4-morpholino-methyl-substituted silicone of formula (V), in which A represents structural unit (I), (II) or (III) or an O-bound oligomeric or polymeric radical including structural units of formulae (I), (II) or (III) or half of a connecting O-atom to a structural unit (III) or represents —OH; wherein * represents a bond to one of the structural units (I), (II) or (III) or an end group B (Si-bound) or D (O-bound); B represents a group —O—Si(CH$_3$)$_3$, —O—Si(CH$_3$)$_2$OH, —O—Si(CH$_3$)$_2$OCH$_3$; D represents a group —Si(CH$_3$)$_3$, —Si(CH$_3$)$_2$OH, —Si(CH$_3$)$_2$OCH$_3$; a, b and c represent integers between 0 and 1000, with the proviso a+b+c>0; m, n and o represent integers between 1 and 1000.

16 Claims, No Drawings

HAIR TREATMENT AGENTS CONTAINING 4-MORPHOLINO-METHYL-SUBSTITUTED SILICONE(S) AND CONDITIONING AGENT(S)

FIELD OF THE INVENTION

The present invention generally relates to hair treatment agents that include specially substituted silicone(s), and to the use of said agents for cleaning and/or caring for hair.

BACKGROUND OF THE INVENTION

Care-providing agents for keratinic fibers influence the natural structure and properties of hair. Subsequent to such treatments, for example, the wet and dry combability of the hair, and its hold and fullness, can be optimized, or the hair can be protected from increased splitting. It has therefore been usual for some time to subject the hair to a special post-treatment. In this the hair is treated, usually in the form of a rinse, with special active agents, for example quaternary ammonium salts or special polymers. Depending on the formulation, this treatment improves the combability, hold, and fullness of the hair, increases shine, and decreases the splitting rate.

In addition, more recently so-called combination preparations have been developed in order to reduce the complexity of the usual multi-step methods, in particular in a context of direct application by users. These preparations additionally include, besides the usual components e.g. for cleaning the hair, active agents that were once reserved for hair post-treatment agents. One utilization step for the consumer is thus eliminated, and at the same time the packaging complexity is reduced because one fewer product is used.

The known active agents cannot, however, meet all requirements to a sufficient extent. A demand therefore continues to exist for active agents or active-agent combinations for cosmetic agents having good care-providing properties and good biodegradability. In surfactant- and/or electrolyte-containing formulations in particular, a demand exists for additional care-providing active agents, which can be incorporated without difficulty into known formulations and whose effect therein is not attenuated as a result of incompatibilities with other ingredients.

Silicones, and among them aminofunctional silicones, are known as care-providing agents in hair treatment agents, and corresponding products are widespread on the market. A demand continues to exist, however, for improving the effects achieved, in particular in terms of the feel, combability, softness, and volume of the hair or hairstyle, and for decreasing the utilization quantities.

It is therefore desirable to furnish silicone-containing hair treatment agents that impart to the hair treated with them even better properties than hair treatment agents having known amodimethicones. It is also desirable to be able to achieve equivalent or better effects even with appreciably reduced utilization quantities. In particular, such hair treatment agents are able to improve the feel, combability, softness, and volume of the hair or hairstyle, and to appreciably minimize the contact angle of water drops present on the treated hair, this being an indication of product performance.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

It has now been found that particularly advantageous results are obtained if specific silicone(s) and conditioning agents are incorporated into hair treatment agents.

A cosmetic composition includes, in a cosmetically acceptable medium, at least one conditioning agent and at least one 4-morpholinomethyl-substituted silicone of formula (V)

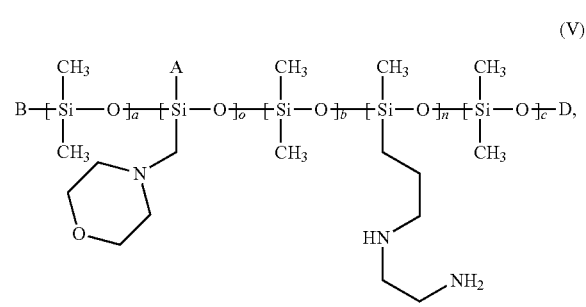

(V)

in which A denotes a structural unit (I), (II), or (III) bound via —O—

(I)

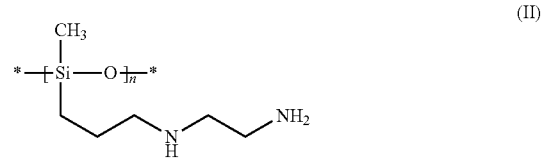

(II)

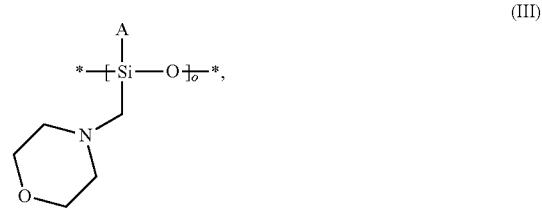

(III)

or an oligomeric or polymeric residue bound via —O— containing structural units of formulas (I), (II), or (III), or half of an oxygen atom connecting to a structural unit (III), or denotes —OH; * denotes a bond to one of the structural units (I), (II), or (III), or denotes a terminal group B (Si-bound) or D (O-bound); B denotes an —OH, —O—Si(CH$_3$)$_3$, —O—Si(CH$_3$)$_2$OH, —O—Si(CH$_3$)$_2$OCH$_3$ group; D denotes an —H, —Si(CH$_3$)$_3$, —Si(CH$_3$)$_2$OH, —Si(CH$_3$)$_2$OCH$_3$ group; a, b, and c denote integers between 0 and 1000, with the provision that a+b+c>0; m, n, and o denote integers between 1 and 1000.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject of the present invention is a cosmetic composition including, in a cosmetically acceptable medium, at least one conditioning agent and at least one 4-morpholinomethyl-substituted silicone of formula (V)

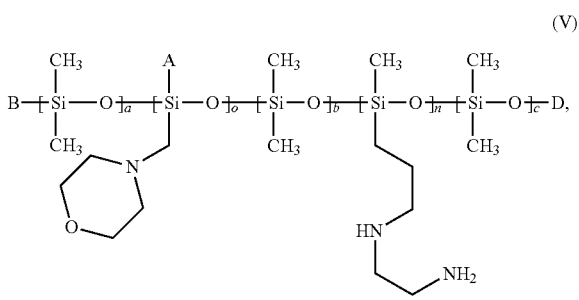
(V)

in which
A denotes a structural unit (I), (II), or (III) bound via —O—

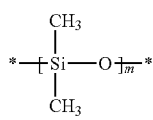
(I)

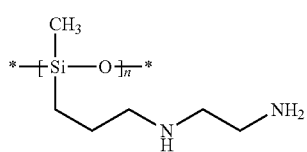
(II)

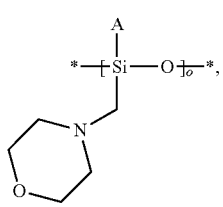
(III)

or an oligomeric or polymeric residue bound via —O— containing structural units of formulas (I), (II), or (III), or half of an oxygen atom connecting to a structural unit (III), or denotes —OH,
* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group,
D denotes an —H, —Si(CH$_3$)$_3$, —Si(CH$_3$)$_2$OH, —Si(CH$_3$)$_2$OCH$_3$ group,
a, b, and c denote integers between 0 and 1000, with the provision that a+b+c>0,
m, n, and o denote integers between 1 and 1000.

The agent according to the present invention is a cosmetic agent. Cosmetic agents preferred according to the present invention are selected from the group of shower gels, shower/bath products, dental cleaning agents, mouthwashes, hair shampoos, hair conditioners, conditioning shampoos, hair sprays, hair rinses, hair therapies, hair packs, hair tonics, permanent wave retention solutions, hair coloring shampoos, hair coloring agents, hair setting agents, hair setting products, hair styling preparations, blow-dry wave lotions, foam setting agents, hair gels, hair waxes, or combinations thereof.

Particularly preferred cosmetic agents according to the present invention serve for the treatment of keratinic fibers and thus represent hair treatment agents. "Hair treatment agents" for purposes of the present invention are, for example, hair shampoos, hair conditioners, conditioning shampoos, hair sprays, hair rinses, hair therapies, hair packs, hair tonics, permanent wave retention solutions, hair coloring shampoos, hair coloring agents, hair setting agents, hair setting products, hair styling preparations, blow-dry wave lotions, foam setting agents, hair gels, hair waxes, or combinations thereof. In view of the fact that men are often reluctant to use multiple different agents and/or multiple utilization steps, agents according to the present invention are preferably those agents which a man uses in any case. Preferred agents according to the present invention are therefore shampoos, conditioning agents, or hair tonics.

The compositions of the invention exhibit improved cosmetic properties (in the case of hair, for example, lightness, softness, ability to untangle, natural feel and an airy hairstyle, brightness); in addition, the effects are more persistent and durable. These effects are, in particular, resistant to many shampoos.

The compositions of the invention moreover result in improved skin suppleness upon application onto the skin (for example by way of a foam bath or shower gel).

The agents according to the present invention include as a first essential ingredient at least one 4-morpholinomethyl-substituted silicone of the structural formula (V). The latter illustrates the fact that the siloxane groups n and o do not obligatorily need to be bound directly to a terminal grouping B or D, respectively. Instead, in preferred formulas (V) a>0 or b>0, and in particularly preferred formulas (V) a>0 and b>0, i.e. the respective terminal grouping B or D is preferably bound to a dimethylsiloxy grouping. In formula (V) the siloxane units a, b, c, n, and o also are preferably statistically distributed.

The silicones used according to the present invention and represented by formula (V) can be trimethylsilyl-terminated at both ends (D=—Si(CH$_3$)$_3$, B=—O—Si(CH$_3$)$_3$), but they can also be dimethylsilylhydroxy-terminated or dimethylsilylmethoxy-terminated at one or two ends. Silicones used particularly preferably in the context of the present invention comprise at least one terminal dimethylsilylhydroxy group, i.e. are selected from silicones in which
B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—Si(CH$_3$)$_2$OH.
These silicones result in exorbitant improvements in the hair properties of hair treated with the agents according to the present invention, in particular in a large decrease in contact angle.

The structural units of formulas (I), (II), and (III) can be present in statistically distributed fashion in the molecule, but the silicones used according to the present invention can also be block copolymers made up of blocks of the individual structural units, wherein the blocks can in turn be present in statistically distributed fashion.

The "*" at the free valences of structural units (I), (II), or (III) denotes a bond to one of the structural units (I), (II), or (III), or denotes a terminal group B (Si-bound) or D (O-bound).

In formula (V), the residue A can denote
a structural unit (I), (II), or (III) bound via —O—, or
an oligomeric or polymeric residue bound via —O— containing structural units of formulas (I), (II), or (III), or
half of an oxygen atom connecting to a structural unit (III), or can denote —OH.

Formula (V) thereby becomes refined to one of formulas (Va), (Vb), (Vc), (Vd), (Ve), or (Vf):

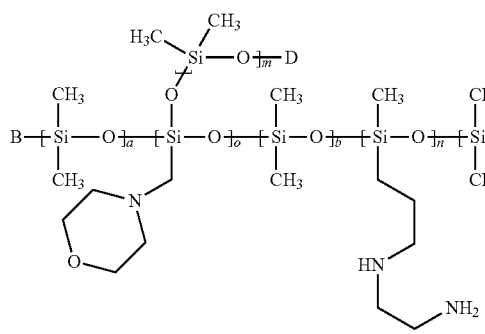
(Va)

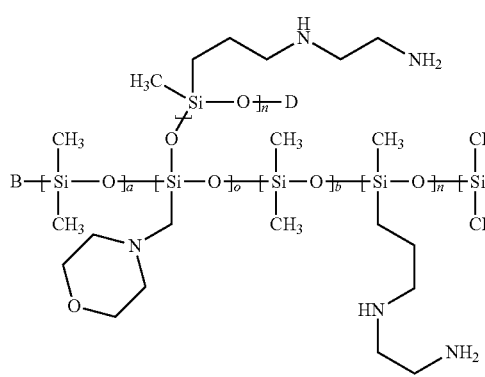
(Vb)

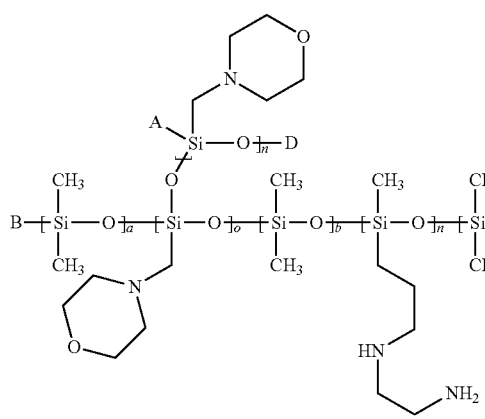
(Vc)

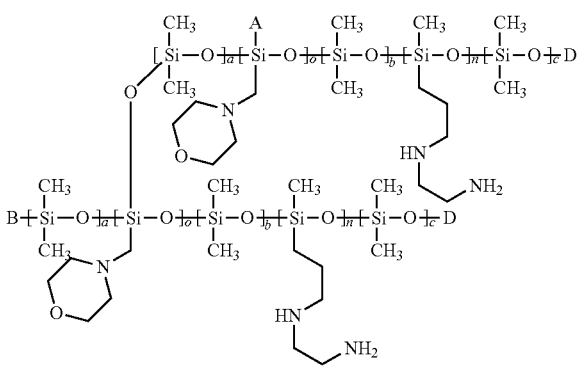
(Vd)

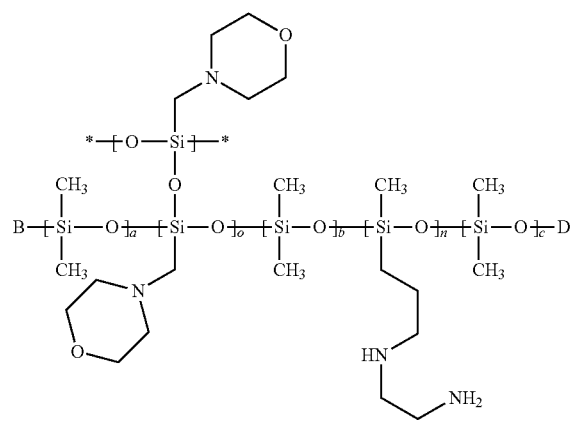
(Ve)

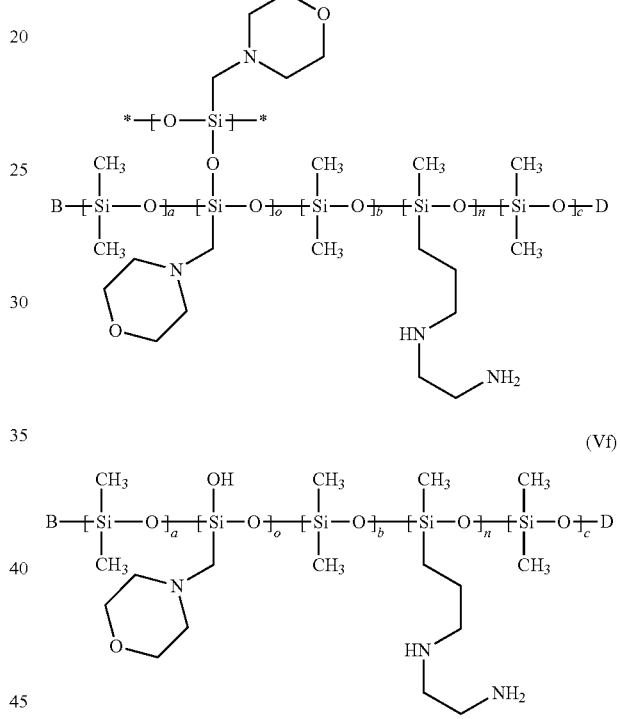
(Vf)

In structural unit (III), the residue A can denote
a structural unit (I), (II), or (III) bound via —O—, or
an oligomeric or polymeric residue bound via —O— containing structural units of formulas (I), (II), or (III), or
half of an oxygen atom connecting to a structural unit (III), or can denote —OH.

In the first case, structural unit (III) becomes one of the structural units (IIIa), (IIIb), or (IIIc):

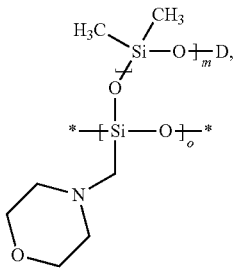
(IIIa)

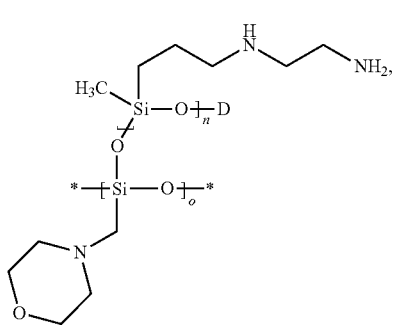
(IIIb)

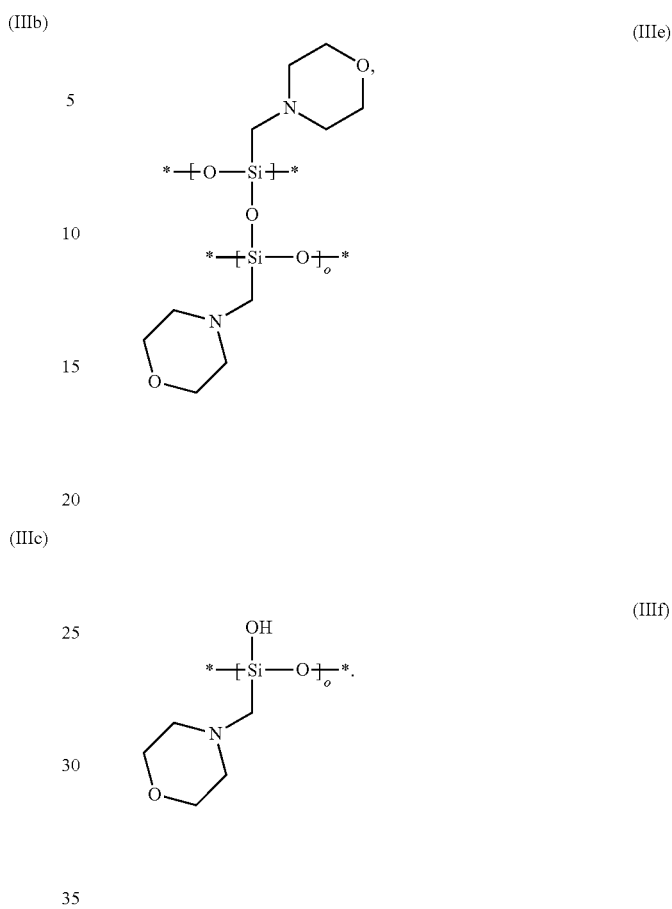
(IIIe)

(IIIc)

(IIIf)

where m=n=o=1, and A and D are respectively as defined above.

In the second case, the indices m, n, and o in the formulas (IIIa), (IIIb), and (IIIc) recited above can denote integers between 2 and 1000. The second case also, however, covers oligomeric or polymeric residues that include at least two different structural units of formulas (I), (II), or (III), as depicted in formula (IIId):

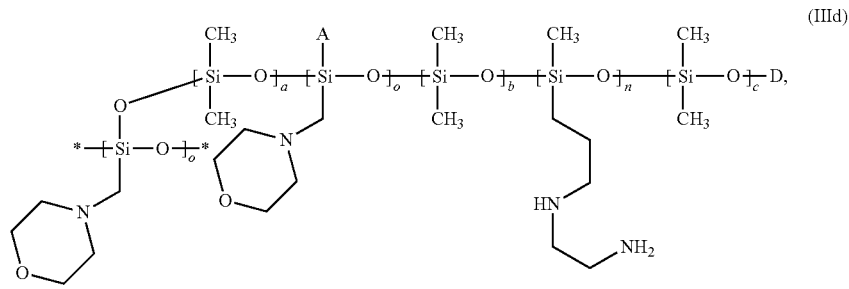
(IIId)

in which a, b, and c denote integers between 0 and 1000, with the provision that a+b+c>0, and n and o denote integers between 1 and 1000.

In the third case, A denotes half of an oxygen atom connecting to a structural unit (III) (depicted in structural unit (IIIe)), or denotes —OH (depicted in structural unit (IIIf)):

Structural unit (III) or the siloxane units o in formula (V) can constitute, via group A, nested or partial cage structures if A denotes half of an oxygen atom connecting to a structural unit (III). Hair treatment agents according to the present invention that include silicones having corresponding 4-morpholinomethyl-substituted silsesquioxane substructures are preferred according to the present invention, since these silicones result in enormously improved combability values and drastically reduced contact angles.

Cosmetic agents preferred according to the present invention are accordingly characterized in that they include at least one 4-morpholinomethyl-substituted silicone that comprises structural units of formula (VI)

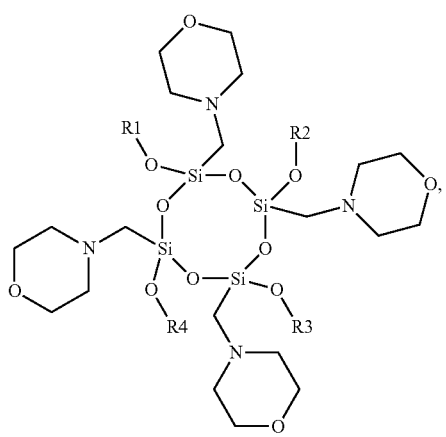

(VI)

In preferred silicones of formula (VI), at least one of the residues R1, R2, R3, or R4 denotes an oligomeric or polymeric residue including structural units of formulas (I), (II), or (III).

In further preferred silicones of formula (VI), at least one of the residues R1, R2, R3, or R4 denotes an oligomeric or polymeric residue including structural units of formulas (I) and (II).

In even further preferred silicones of formula (VI), at least one of the residues R1, R2, R3, or R4 denotes an oligomeric or polymeric residue including structural units of formulas (I) and (II) and (III).

At least one of the residues R1, R2, R3, or R4 preferably denotes an —[—Si(CH$_3$)$_2$—O]$_m$ grouping, i.e. an oligomer or polymer of structural unit (I). In addition, structural unit (II) or an oligomer or polymer thereof preferably is never bound in the molecule alone, but instead always in a statistical distribution with further structural units of formula (I) as one of the residues R1, R2, R3, or R4.

Preferred silicones of formula (VI) can be described by formula (VI a)

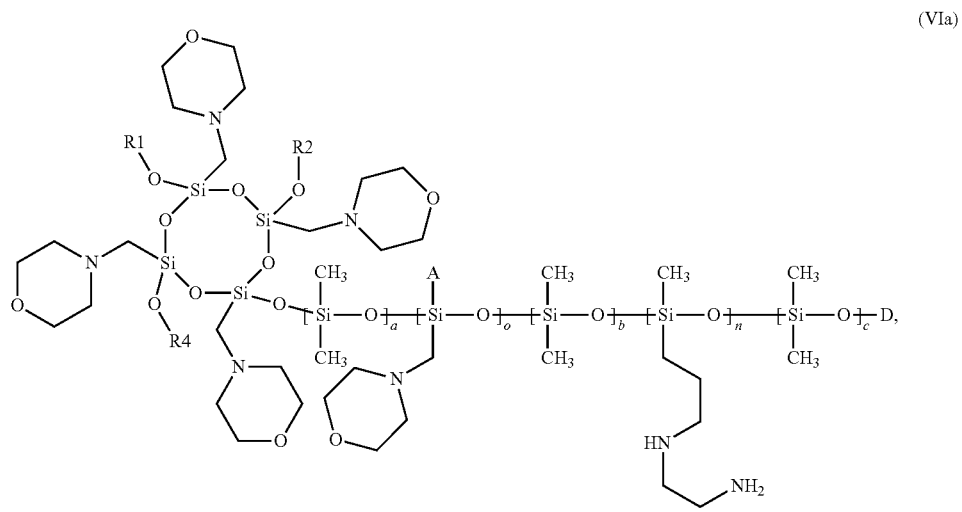

(VIa)

in which

R1, R2, R3, and R4 mutually independently denote —H, —CH$_3$, a group D, a structural unit (I), (II), or (III), or an oligomeric or polymeric residue including structural units of formulas (I), (II), or (III), or two of the residues R1, R2, R3, and R4 denote a structural unit —Si(R6)(R5)-, where R5=—CH$_3$ or a structural unit of formula (I) or (II) or (III) or an oligomeric or polymeric residue including structural units of formulas (I), (II), or (III), R6=—OH, —CH$_3$, or a structural unit of formula (I) or (II) or (III) or an oligomeric or polymeric residue including structural units of formulas (I), (II), or (III).

in which

R1, R2, and R4 mutually independently denote —H, —CH$_3$, a group D, a structural unit (I), (II), or (III), or an oligomeric or polymeric residue including structural units of formulas (I), (II), or (III), or two of the residues R1, R2, and R4 denote a structural unit —Si(R6)(R5)-, where R5=—CH$_3$ or a structural unit of formula (I) or (II) or (III) or an oligomeric or polymeric residue including structural units of formulas (I), (II), or (III), R6=—OH, —CH$_3$, or a structural unit of formula (I) or (II) or (III) or an oligomeric or polymeric residue including structural units of formulas (I), (II), or (III), A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH₃)₃, —Si(CH₃)₂OH, —Si(CH₃)₂OCH₃ group, a, b, and c denote integers from 0 to 1000, with the provision that a+b+c>0, n, and o denote integers from 1 to 1000.

Further preferred silicones of formula (VI) can be described by formula (VI b)

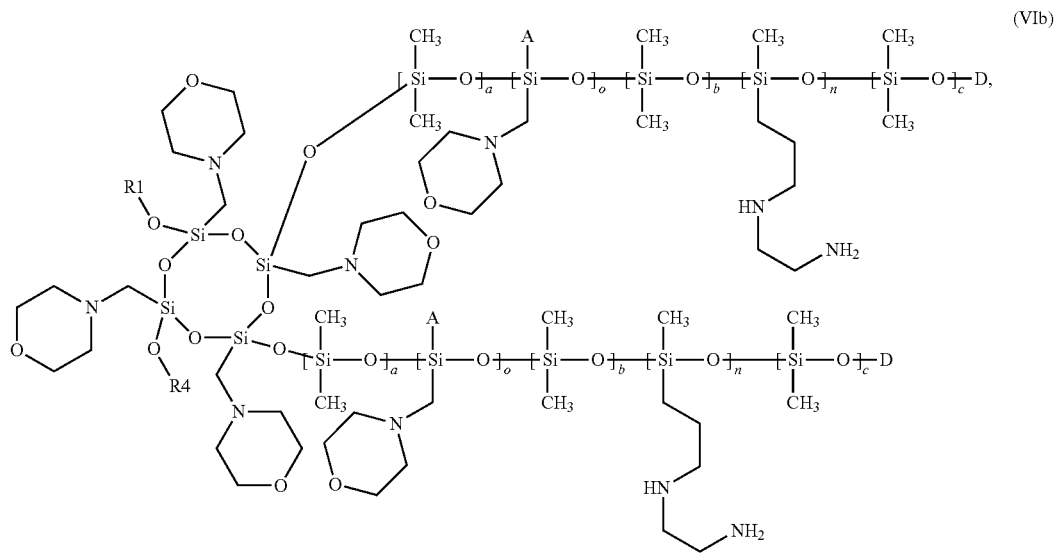

(VIb)

in which the residues and indices are as defined above.

Particularly preferred silicones of formula (VI) can be described by formula (VI c)

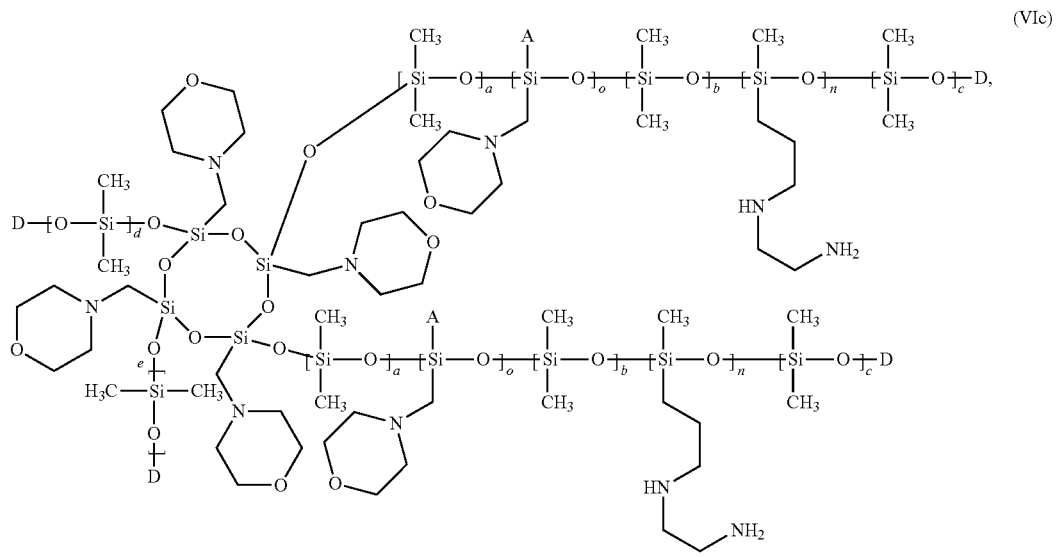

(VIc)

in which the residues and indices are as defined above, and the indices d and e denote integers between 0 and 1000.

In formulas (VI a), (VI b), and (VI c), at least one of the groupings D preferably denotes —Si(CH₃)₂OH.

The silsesquioxane structures can be even more pronounced in the silicones used according to the present invention, which intensifies the advantageous effects. Particularly preferred cosmetic agents according to the present invention are characterized in that they include at least one 4-morpholinomethyl-substituted silicone that comprises structural units of formula (VII)

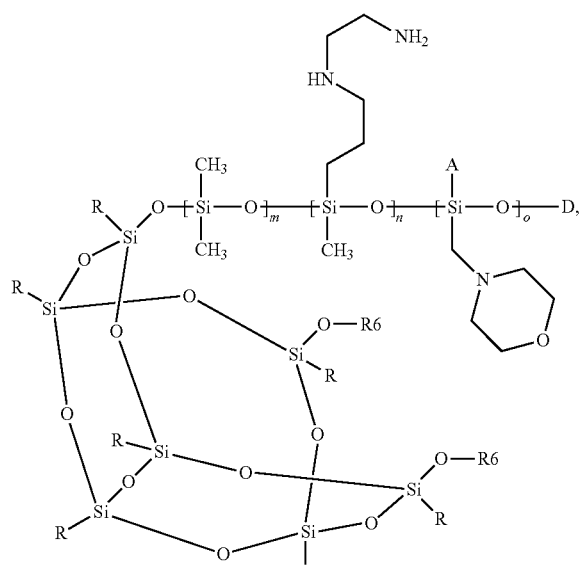

(VII)

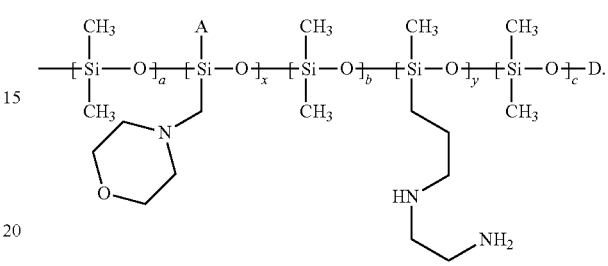

in which
A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH,
D denotes an —H, —Si(CH$_3$)$_3$, —Si(CH$_3$)$_2$OH, —Si(CH$_3$)$_2$OCH$_3$ group,
R denotes a 4-morpholinomethyl residue,
R6 denotes —H or the grouping wherein the siloxane units m, n, and o and a, b, c, x, and y are present in statistically distributed fashion.

Particularly preferred cosmetic agents according to the present invention include at least one silicone of the following formula (VII a)

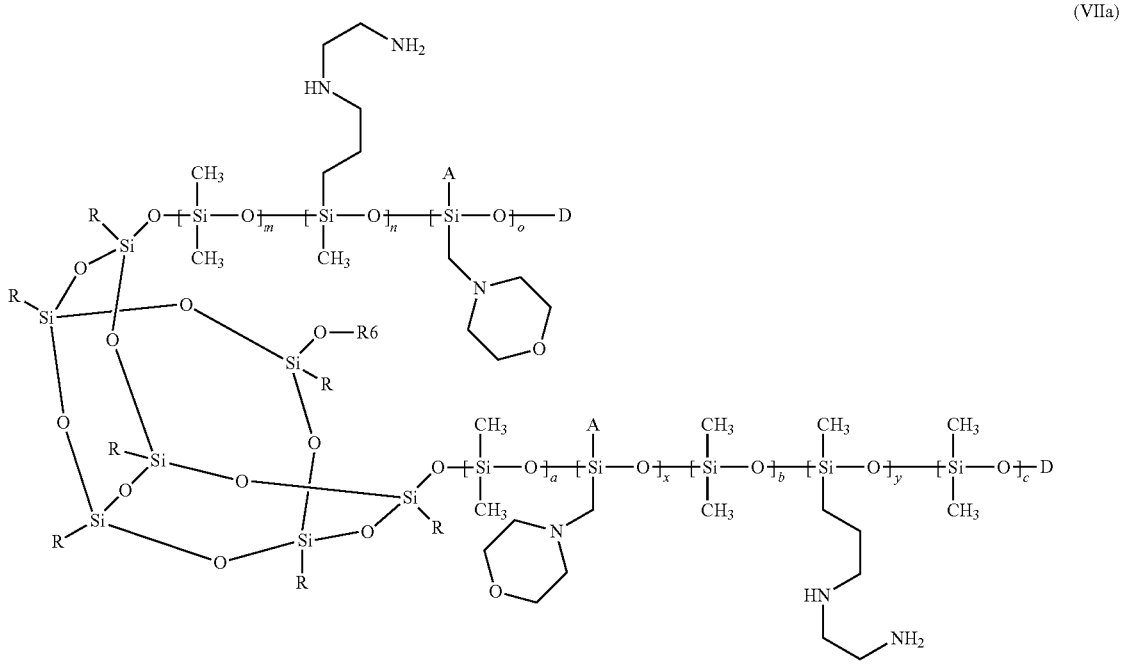

(VIIa)

with the definitions as for formula (VII).

Very particularly preferred cosmetic agents according to the present invention include at least one silicone of the following formula (VII b)

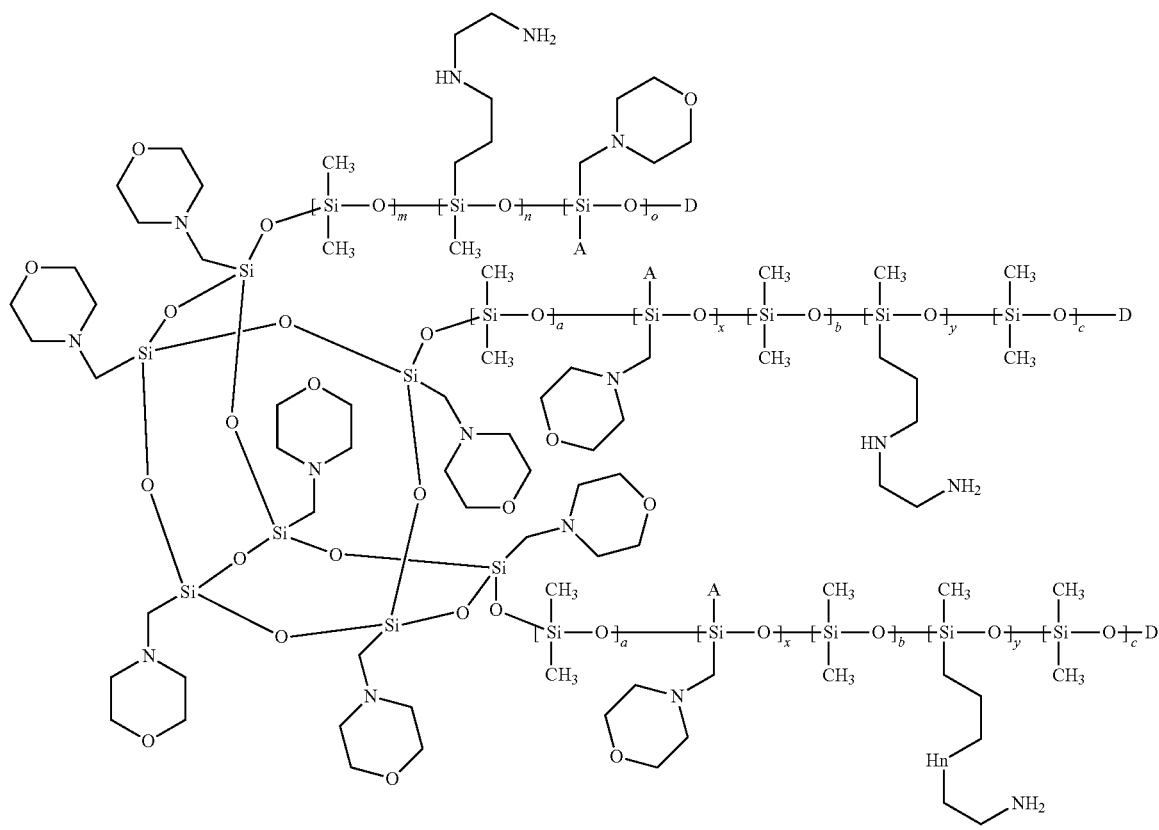

(VIIb)

with the definitions as for formula (VII).

In formulas (VII), (VII a), and (VII b), the bridging oxygen atoms between the morpholinomethyl-substituted silicon atoms can also be supplemented by an —[—Si(CH$_3$)$_2$—O]$_m$ grouping, i.e. an oligomer or polymer of structural unit (I). Corresponding hair treatment agents according to the present invention which include at least one 4-morpholinomethyl-substituted silicone that comprises structural units of formula (VIII)

(VIII)

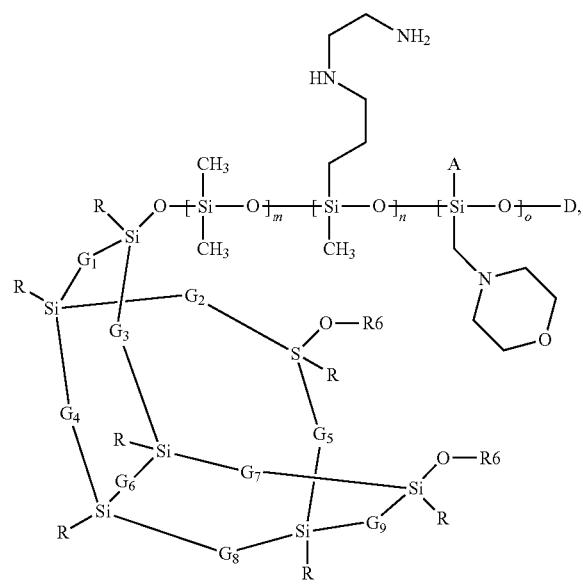

in which

A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH$_3$)$_3$, —Si(CH$_3$)$_2$OH, —Si(CH$_3$)$_2$OCH$_3$ group, G1 to G9 mutually independently denote —O— or an —[—Si(CH$_3$)$_2$—O]$_m$ group where m=1 to 200, R denotes a 4-morpholinomethyl residue, R6 denotes —H or the grouping

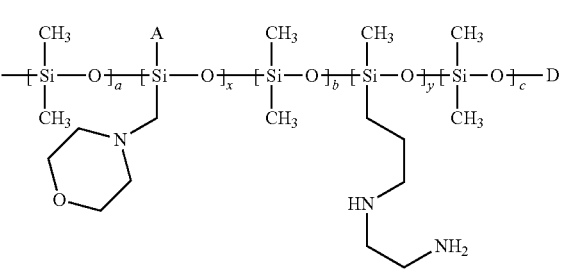

wherein the siloxane units m, n, and o, and a, b, c, x, and y, are present in statistically distributed fashion are preferred.

Particularly preferred cosmetic agents according to the present invention include at least one silicone of the following formula (VIII a)

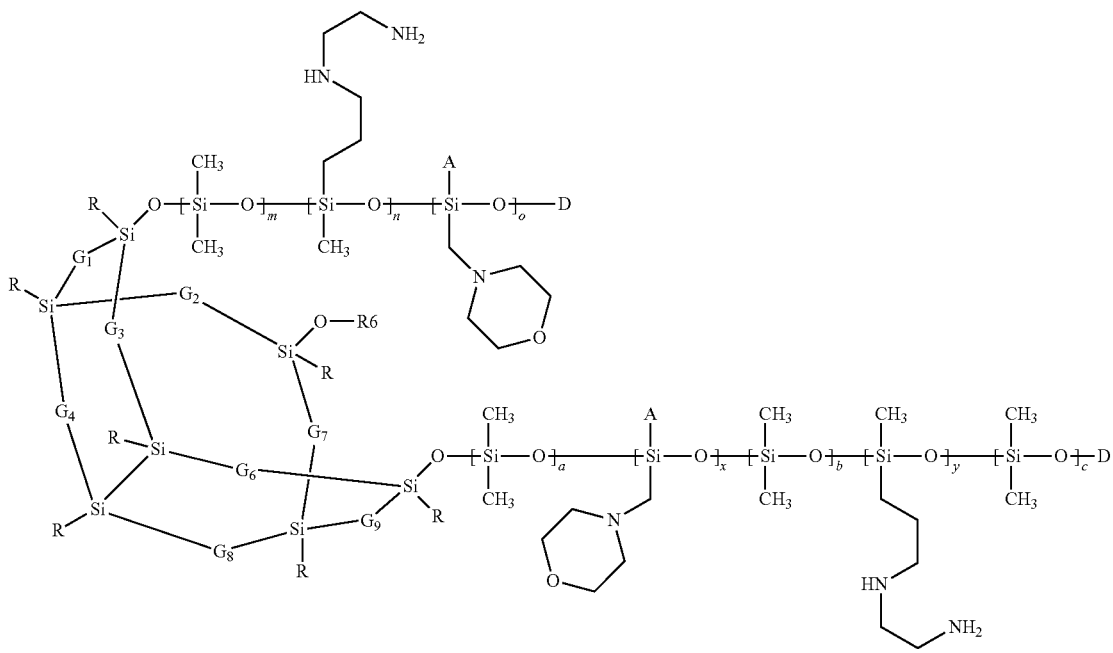
(VIIIa)
with the definitions as for formula (VIII).
Very particularly preferred cosmetic agents according to the present invention include at least one silicone of the following formula (VIII b)
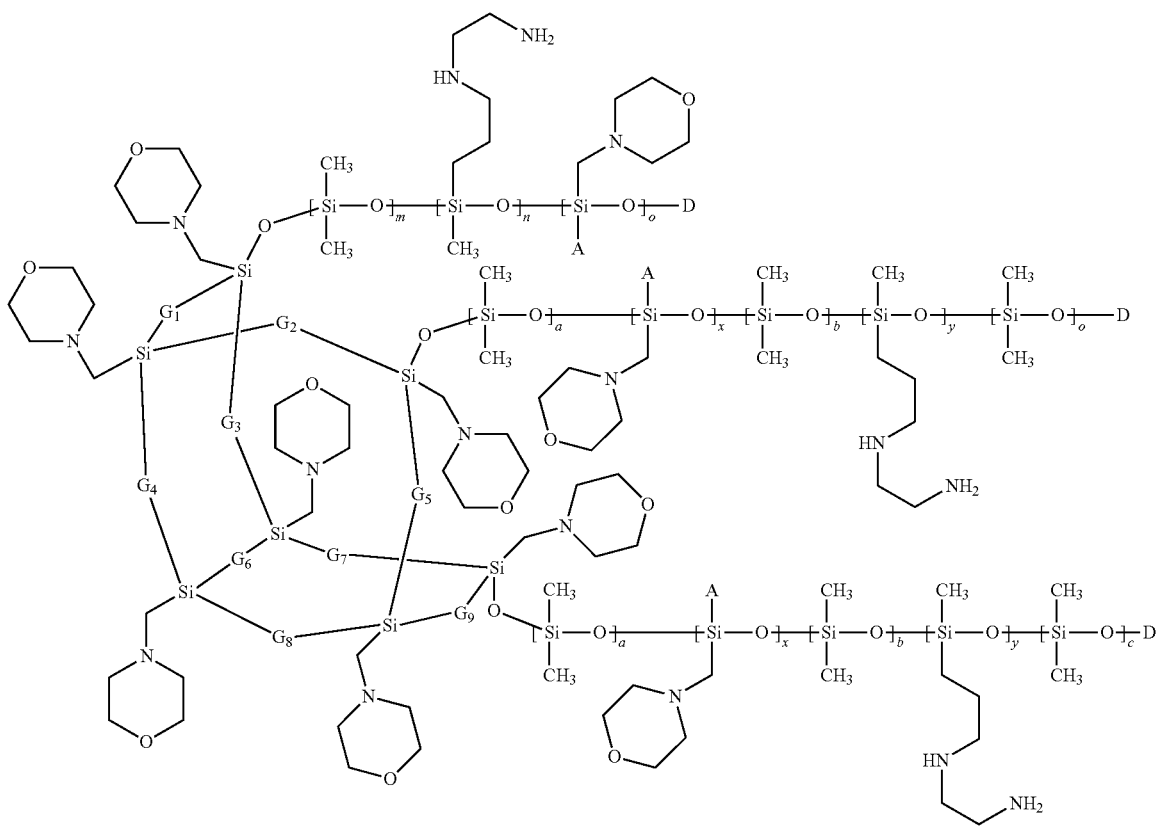
(VIIIb)
with the definitions as for formula (VIII).

Regardless of which special 4-morpholinomethyl-substituted silicone is employed in the cosmetic agents according to the present invention, agents according to the present invention that include a 4-morpholinomethyl-substituted silicone in which more than 50 mol % of the structural units are dimethylsiloxy units, i.e. in which structural unit (I) makes up at least half of all structural units of the silicone used, are preferred.

In other words, silicones in which m>(n+o) or (a+b+c)>(n+o) are preferred.

Even further preferred cosmetic agents include a 4-morpholinomethyl-substituted silicone in which more than 90 mol % of the structural units are dimethylsiloxy units, i.e. in which structural unit (I) makes up at least nine tenths of all structural units of the silicone used.

In other words, silicones in which m>10(n+o) or (a+b+c)>10(n+o) are preferred.

Even further preferred cosmetic agents include a 4-morpholinomethyl-substituted silicone in which more than 98 mol % of the structural units are dimethylsiloxy units, i.e. in which structural unit (I) makes up at least ninety-eight hundredths of all structural units of the silicone used.

In other words, silicones in which m>50(n+o) or (a+b+c)>50(n+o) are preferred.

Even further preferred cosmetic agents include a 4-morpholinomethyl-substituted silicone in which more than 98.5 mol % of the structural units are dimethylsiloxy units, i.e. in which structural unit (I) makes up at least nine hundred eighty-five thousandths of all structural units of the silicone used.

In other words, silicones in which m>75(n+o) or (a+b+c)>75(n+o) are preferred.

Even further preferred cosmetic agents include a 4-morpholinomethyl-substituted silicone in which more than 99 mol % of the structural units are dimethylsiloxy units, i.e. in which structural unit (I) makes up at least ninety-nine hundredths of all structural units of the silicone used.

In other words, silicones in which m>100(n+o) or (a+b+c)>100(n+o) are preferred.

In summary, preferred cosmetic agents according to the present invention are characterized in that they include at least one 4-morpholinomethyl-substituted silicone in which $m>(n+o)$ or $(a+b+c)>(n+o)$, preferably $m>10(n+o)$ or $(a+b+c)>10(n+o)$, particularly preferably $m>50(n+o)$ or $(a+b+c)>50(n+o)$, more preferably $m>75(n+o)$ or $(a+b+c)>75(n+o)$, and in particular $m>100(n+o)$ or $(a+b+c)>100(n+o)$.

The 4-morpholinomethyl-substituted silicone(s) can be employed in varying quantities depending on the intended use of the agents according to the present invention. Preferred cosmetic agents according to the present invention are characterized in that they include, based on their weight, 0.00001 to 10 wt %, preferably 0.0001 to 7.5 wt %, particularly preferably 0.001 to 5 wt %, more preferably 0.01 to 3 wt %, and in particular 0.1 to 1 wt % 4-morpholinomethyl-substituted silicone(s).

It has become apparent that the effect of the silicones employed according to the present invention can be further increased if specific nonionic components are likewise included in the agents according to the present invention. These nonionic components furthermore have positive effects on the shelf stability of the agents according to the present invention. Nonionic components that are particularly suitable here are ethoxylates of decanol, undecanol, dodecanol, tridecanol, etc. Ethoxylated tridecanols have proven to be particularly suitable, and are incorporated with particular preference into the agents according to the present invention. Cosmetic compositions particularly preferred according to the present invention include, based on their weight, 0.00001 to 5 wt %, preferably 0.0001 to 3.5 wt %, particularly preferably 0.001 to 2 wt %, more preferably 0.01 to 1 wt %, and in particular 0.1 to 0.5 wt % branched ethoxylated tridecanol (INCI name: Trideceth-5) or α-isotridecyl-ω-hydroxypolyglycol ether (INCI name: Trideceth-10), or mixtures thereof.

Morpholinomethyl-substituted silicone(s) preferred according to the present invention comprise both hydroxy groups and alkoxy groups. Cosmetic compositions particularly preferred according to the present invention include hydroxy-terminated 4-morpholinomethyl-substituted silicone(s) in which the molar ratio of hydroxy to alkoxy is in the range from 0.2:1 to 0.4:1, preferably in the range from 1:0.8 to 1:1.1.

The average molecular weight of the silicone is preferably from 2000 to 200,000, and even more preferably from 5000 to 100,000, in particular 10,000 to 50,000 dalton. Cosmetic compositions in which the weight-average molar mass of the 4-morpholinomethyl-substituted silicone of formula (V) included therein is in the range from 2000 to 1,000,000 $gmol^{-1}$, preferably in the range from 5000 to 200,000 $gmol^{-1}$, are preferred.

The average molecular weights of aminosubstituted silicones are measurable, for example, by gel permeation chromatography (GPC) at room temperature in polystyrene. Styragel μ columns can be selected as columns, THF as an eluent, and 1 ml/min as a flow rate. Detection is accomplished preferably by refractometry using a UV meter.

The 4-morpholinomethyl-substituted silicone(s) of formula (V) are used preferably as an oil-in-water emulsion. The oil-in-water emulsion can include one or more surfactants. The surfactants can be of any kind, preferably cationic and/or nonionic. The number-average average size of the silicone droplets in the emulsion is preferably between 3 nm and 500 nm, particularly preferably between 5 nm and 60 nm (inclusive), and in particular between 10 nm and 50 nm (inclusive).

Cosmetic compositions according to the present invention in which the 4-morpholinomethyl-substituted silicone of formula (V) is present in the form of an oil-in-water emulsion in which the number-average size of the silicone particles in the emulsion is in the range from 3 to 500 nm, preferably in the range from 5 to 60 nm, are preferred according to the present invention.

The 4-morpholinomethyl-substituted silicones of formula (V) are preferably selected so that the contact angle of human hair with water, after treatment with a composition that includes 2% (active agent) of the aforesaid silicone, is between 90° and 180° (inclusive), preferably between 90 and 130° (inclusive).

A further essential constituent of the compositions according to the present invention is a conditioning agent.

In the context of the present invention, the term "conditioning agent" signifies any compound that is capable of improving at least one cosmetic property of keratinic material such as hair, for example the softness, suppleness, feel, ability to detangle, or static charging capability. The at least one conditioning agent can be water-soluble or water-insoluble.

The at least one conditioning agent can be selected, for example, from synthetic oils such as polyolefins, mineral oils, vegetable oils, fluoro and perfluoro oils, natural and synthetic waxes, ceramides, carboxylic acid esters, silicones that are different from the morpholinomethyl-substituted silicones employed according to the present invention, anionic polymers, nonionic polymers, cationic polymers, amphoteric polymers, cationic proteins and protein hydrolysates, cationic surfactants, etc.

Cosmetic compositions preferred according to the present invention are characterized in that the conditioning agents are selected from among synthetic oils, mineral oils, vegetable oils, fluorinated or perfluorinated oils, natural or synthetic waxes, compounds of the ceramide type, carboxylic acid esters, silicones different from the silicones of formula (V), anionic polymers, nonionic polymers, cationic polymers, amphoteric polymers, cationic proteins, cationic protein hydrolysates, and cationic surface-active substances, as well as mixtures of these various compounds.

Water-insoluble conditioning agents can be solid, liquid, or pasty at 25° C. and 1013 mbar, and can be present as oils, waxes, resins, or gums.

Water-insoluble conditioning agents can also be present in a dispersed form that preferably exhibits number-average particle or droplet sizes from 2 nm to 100 μm, preferably from 30 nm to 20 μm. The number-average particle size is determined here by means of a granulometer. Water-insoluble conditioning agents dissolve in water at 25° C. at a proportion of less than 0.1 wt %, i.e. they do not form macroscopically isotropic, transparent solutions under such conditions.

Synthetic oils, for example polyolefins, in particular poly-alpha-olefins, can be selected from: poly-α-olefins of the hydrogenated or non-hydrogenated polybutene type or the hydrogenated or non-hydrogenated polyisobutene type. Isobutylene oligomers having molar masses of less than 1000, and mixtures thereof with polyisobutylenes having molar masses greater than 1000, for example from 1000 to 15,000, can preferably be used.

Corresponding commercial products are, for example, Permethyl® 99A, 101 A, 102A, 104 A (n=16) and 106 A (n=38) of Presperse, Inc., or the Arlamol® HD products (n=3) of ICI (wherein n identifies the degree of polymerization).

Poly-α-olefins of the hydrogenated or non-hydrogenated polydecene type, which are marketed under the designations Ethylflo® (Ethyl Corp.) and Arlamol® PAO (ICI), are also usable.

Cosmetic compositions preferred according to the present invention are characterized in that the synthetic oil(s) are polyolefins of the hydrogenated or non-hydrogenated polybutene type or of the hydrogenated or non-hydrogenated polydecene type.

Cosmetic oils are usable with particular preference as conditioning agents. These oily substances preferably have a melting point lower than 50° C., particularly preferably lower than 45° C., very particularly preferably lower than 40° C., highly preferably lower than 35° C., and most preferably the cosmetic oils are flowable at a temperature lower than 30° C. These oils will be more specifically defined and described below.

Included among the natural and synthetic cosmetic oils are, for example:

Vegetable oils. Examples of such oils are sunflower oil, olive oil, soy oil, rapeseed oil, almond oil, jojoba oil, orange oil, wheat germ oil, peach-kernel oil, and the liquid components of coconut oil. Also suitable, however, are other triglyceride oils such as the liquid components of beef tallow, as well as synthetic triglyceride oils.

Liquid paraffin oils, isoparaffin oils, and synthetic hydrocarbons, as well as di-n-alkyl ethers having a total of between 12 and 36 carbon atoms, in particular 12 to 24 carbon atoms, for example di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether, and n-hexyl-n-undecyl ether, as well as ditert-butyl ether, diisopentyl ether, di-3-ethyldecyl ether, tert-butyl-n-octyl ether, isopentyl-n-octyl ether, and 2-methylpentyl-n-octyl ether. The compounds 1,3-di-(2-ethylhexyl)cyclohexane (Cetiol® S) and di-n-octyl ether (Cetiol® OE), available as commercial products, can be preferred.

Ester oils. "Ester oils" are to be understood as esters of $C_6$ to $C_{30}$ fatty acids with $C_2$ to $C_{30}$ fatty alcohols. The monoesters of fatty acids with alcohols having 2 to 24 carbon atoms are preferred. Examples of fatty-acid components used in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid, and erucic acid, as well as industrial mixtures thereof that occur, for example, upon high-pressure hydrogenation of natural fats and oils, or upon oxidation of aldehydes from Roelen oxosynthesis or dimerization of unsaturated fatty acids. Examples of the fatty-alcohol components in the ester oils are isopropyl alcohol, capronyl alcohol, capryl alcohol, 2-ethylhexyl alcohol, caprinyl alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, eleostearyl alcohol, arachyl alcohol, gadoleyl alcohol, behenyl alcohol, erucyl alcohol, and brassidyl alcohol, as well as industrial mixtures thereof that occur, for example, upon high-pressure hydrogenation of natural fats and oils, or upon oxidation of aldehydes from Roelen oxosynthesis or dimerization of unsaturated fatty alcohols. Isopropyl myristate (Rilanit® IPM), isononanoic acid C16-18 alkyl esters (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are particularly preferred according to the present invention.

dicarboxylic acid esters such as di-n-butyl adipate, di-(2-ethylhexyl) adipate, di-(2-ethylhexyl)succinate, and diisotridecyl acelaate, as well as diol esters such as ethylene glycol dioleate, ethylene glycol diisotridecanoate, propylene glycol di-(2-ethylhexanoate), propylene glycol diisostearate, propylene glycol dipelargonate, butanediol diisostearate, neopentyl glycol dicaprylate, symmetrical, asymmetrical, or cyclic esters of carbonic acid with fatty alcohols, described e.g. in German Application 197 56 454, glycerol carbonate or dicaprylyl carbonate (Cetiol® CC), fatty acid triesters of saturated and/or unsaturated linear and/or branched fatty acids with glycerol, fatty acid partial glycerides, i.e. monoglycerides, diglycerides, and industrial mixtures thereof. When industrial products are used, small quantities of triglycerides may still be present for manufacturing-related reasons. The partial glycerides preferably conform to formula (D4-I),

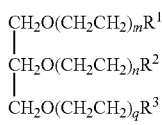

(D4-I)

in which $R^1$, $R^2$ and $R^3$ mutually independently denote hydrogen or a linear or branched, saturated and/or unsaturated acyl residue having 6 to 22, preferably 12 to 18 carbon atoms, with the provision that at least one of these groups denotes an acyl residue and at least one of these groups denotes hydrogen. The sum (m+n+q) denotes 0 or numbers from 1 to 100, preferably 0 or 5 to 25. Preferably $R^1$ denotes an acyl residue and $R^2$ and $R^3$ denote hydrogen, and the sum (m+n+q) is 0. Typical examples are mono- and/or diglycerides based on hexanoic acid, octanoic acid, 2-ethylhexanoic acid, decanoic acid, lauric acid, isotridecanoic acid, myristic acid, palmitic acid, palmoleic acid, stearic acid, isostearic acid, oleic acid, elaidic acid, petroselinic acid, linoleic acid, linolenic acid, eleostearic acid, arachidic acid, gadoleic acid, behenic acid and erucic acid, as well as industrial mixtures thereof. Oleic acid monoglycerides are preferably used.

Natural oils used are, for example, amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, blackcurrant seed oil, jojoba oil, cocoa butter, linseed oil, macadamia nut oil, corn oil, almond oil, marula oil, evening primrose oil, olive oil, palm oil, rapeseed oil, rice oil, sea buckthorn pulp oil, sea buckthorn seed oil, sesame oil, shea butter, soy oil, sunflower oil, grapeseed oil, walnut oil, or wild rose oil.

Preferred natural oils include at least the fatty acids palmitic acid, stearic acid, and linoleic acid. Particularly preferred natural oils include the fatty acids palmitic acid, stearic acid, and linoleic acid in a total quantity of at least 50 wt % of the fatty acids. A "+" sign after the respective oils in the table above identifies these particularly preferred natural oils. Very particularly preferred oils are furthermore notable for an additional squalene content. Most-preferred natural oils and mixtures thereof also comprise a proportion of linolenic acids.

The teaching of the present invention of course also comprises the fact that at least two of the natural oils listed in the table above can be mixed with one another. In this case, however, the natural oils must be selected in such a way that the sum of the fatty acids palmitic acid, stearic acid, and linoleic acid yields at least 50 wt % of the sum of the total fatty acids. Preferred mixtures of the natural oils are amaranth seed oil with at least one sea buckthorn oil, amaranth seed oil with shea butter, amaranth seed oil with camelina oil, amaranth seed oil with olive oil, amaranth seed oil with macadamia nut oil, olive oil with at least one sea buckthorn oil, olive oil with camelina oil, olive oil with shea butter, macadamia nut oil and at least one sea buckthorn oil, macadamia nut oil with shea butter. More than at most three of the natural oils should not, however, be mixed with one another.

Argan oil is one of the particularly preferred natural oils.

Preferred cosmetic compositions according to the present invention are characterized in that the vegetable oil(s) are selected from sunflower oil, corn oil, soy oil, avocado oil, jojoba oil, pumpkin seed oil, grapeseed oil, sesame oil, hazelnut oil, fish oils, glycerol tricaprocaprylate, or vegetable or animal oils of the formula $R_9COOR_{10}$ in which $R_9$ signifies the residue of a higher fatty acid having 7 to 29 carbon atoms, and $R_{10}$ signifies a linear or branched hydrocarbon chain having 3 to 30 carbon atoms, natural or synthetic essential oils.

Natural or synthetic waxes (Fatwax) that can be used according to the present invention are solid paraffins or isoparaffins, carnauba waxes, beeswaxes, candelilla waxes, ozocerites, ceresin, spermaceti, sunflower wax, fruit waxes such as apple wax or citrus wax, microcrystalline waxes made from PE or PP. Such waxes are obtainable, for example, via Kahl & Co., Trittau.

Preferred cosmetic compositions according to the present invention are characterized in that the wax or waxes are selected from carnauba wax, candelilla wax, Alpha wax, paraffin wax, ozocerite, vegetable waxes, animal waxes, polyethylene waxes, or polyolefin waxes.

The quantity used is 0.1 to 50 wt % based on the total agent, preferably 0.1 to 20 wt %, and particularly preferably 0.1 to 15 wt %, based on the total agent.

Compounds of the ceramide type can be selected, for example, from natural and synthetic ceramides, glycoceramides, pseudoceramides, and neoceramides. Preferred representatives of these groups are 2-N-linoleoylaminooctadecane-1,3-diol, 2-N-oleoylaminooctadecane-1,3-diol, 2-N-palmitoylaminooctadecane-1,3-diol, 2-N-stearoylaminooctadecane-1,3-diol, 2-N-behenoylaminooctadecane-1,3-diol, 2-N-[2-hydroxypalmitoyl]aminooctadecane-1,3-diol, 2-N-stearoylaminooctadecane-1,3,4-triol and such as N-stearoylphytosphingosine, 2-N-palmitoylaminohexadecane-1,3-diol, bis(N-hydroxyethyl-N-cetyl)malonamide, N-(2-hydroxyethyl)-N-(3-cetyloxy-2-hydroxypropyl)cetylamide, N-docosanoyl-N-methyl-D-glucamine, and mixtures of these compounds.

Preferred cosmetic compositions according to the present invention are characterized in that the compounds of the ceramide type are selected from:
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol,
2-N-palmitoylaminohexadecane-1,3-diol,
bis(N-hydroxyethyl-N-cetyl)malonamide,
N-(2-hydroxyethyl)-N-(3-cetyloxy-2-hydroxypropyl)amide of cetylic acid,
N-docosanoyl-N-methyl-D-glucamine,
or mixtures of these compounds.

"Fatty alcohols" are understood as primary aliphatic alcohols of the formula $R^1OH$ in which $R^1$ denotes an aliphatic linear or branched hydrocarbon residue having 6 to 22 carbon atoms and 0 and/or 1, 2, or 3 double bonds. Typical examples are hexanol, octanol, 2-ethylhexyl alcohol, decanol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, eleostearyl alcohol, arachyl alcohol, gadoleyl alcohol, behenyl alcohol, erucyl alcohol, and brassidyl alcohol, as well as industrial mixtures thereof that occur, for example, upon high-pressure hydrogenation of industrial methyl esters based on fats and oils or aldehydes from Roelen oxosynthesis, and as a monomer fraction upon dimerization of unsaturated fatty alcohols. Industrial fatty alcohols having 12 to 18 carbon atoms, for example coconut, palm, palm kernel, or tallow fatty alcohol, are preferred. Alkoxylated fatty alcohols having 1 to 15 mol alkylene oxide, or polyglycerated compounds having 1 to 6 mol glycerol, can also be used as conditioning agents.

Monocarboxylic acid esters can also be used with particular preference as conditioning agents. These esters are selected, for example, from linear or branched, saturated or unsaturated aliphatic $C_1$ to $C_{26}$ monoesters of linear or branched, saturated or unsaturated $C_1$ to $C_{26}$ alcohols, wherein the total number of carbon atoms in the esters is 10 or more.

Particularly preferred conditioning agents are dehydroabietyl behenate; octyldodecyl behenate; isocetyl behenate; cetyl lactate; $C_{12}$ to $C_{15}$ alkyl lactates; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate, isocetyl laurate, isocetyl stearate, isodecyl octanoate, isodecyl oleate, isononyl isononanoate, isostearyl palmitate, methylacetyl ricinoleate, myristyl stearate, octyl isononanoate, 2-ethylhexyl isononate, octyl palmitate, octyl pelargonate, octyl stearate, octyldodecyl erucate, oleyl erucate, ethyl and isopropyl palmitates, 2-ethylhexyl palmitate, 2-octyldecyl palmitate, alkyl myristates such as isopropyl, butyl, cetyl, and 2-octyldodecyl myristate, hexyl stearate, butyl stearate, isobutyl stearate, dioctyl malate, hexyl laurate, and 2-hexyldecyl laurate.

$C_4$ to $C_{22}$ di- or tricarboxylic acid esters of $C_1$ to $C_{22}$ alcohols, and mono-, di-, or tricarboxylic acid esters of $C_2$ to $C_{26}$ di-, tri- tetra-, or pentahydroxyalcohols can likewise be used.

To be recited here are diethyl sebacate, diisopropyl sebacate, diisopropyl adipate, di-n-propyl adipate, dioctyl adipate, diisostearyl adipate, dioctyl maleate, glyceryl undecylenate, octyldodecylstearoyl stearate, pentaerythrityl monoricinoleate, pentaerythrityl tetraisononanoate, pentaerythrityl tetrapelargonate, pentaerythrityl tetraisostearate, pentaerythrityl tetraoctanoate, propylene glycol dicaprylate dicaprate, tridecyl erucate, triisopropyl citrate, triisostearyl citrate, glyceryl trilactate, glyceryl trioctanoate, trioctyldodecyl citrate, and trioleyl citrate.

Among the esters recited above, some are particularly preferred. Cosmetic compositions according to the present invention in which the carboxylic acid esters are selected from ethyl palmitate and isopropyl palmitate, 2-ethylhexyl palmitate, 2-octyldecyl palmitate, alkyl myristates, hexyl stearate, butyl stearate, isobutyl stearate; dioctyl malate, hexyl laurate, 2-hexyldecyl laurate, isononyl isononanoate, and cetyl octanoate are preferred according to the present invention.

Silicones that differ from the silicones of formula (V) employed according to the present invention can also be used as conditioning agents.

Agents preferred according to the present invention are characterized in that they include at least one further silicone. Particularly preferred cosmetic compositions according to the present invention are characterized in that they are nonvolatile polyorganosiloxanes, different from the silicones of formula (V), that are selected from polyalkylsiloxanes, polyarylsiloxanes, polyalkylarylsiloxanes, silicone rubbers, silicone resins, polyorganosiloxanes modified with organofunctional groups, and mixtures thereof.

Very particularly preferred cosmetic compositions according to the present invention are characterized in that
(a) polyalkylsiloxanes are selected from among:
  polydimethylsiloxanes having terminal trimethylsilyl groups;
  polydimethylsiloxanes having terminal dimethylsilanol groups;
  polyalkyl ($C_{1-20}$) siloxanes;
(b) polyarylsiloxanes are selected from among:
  polydimethylmethylphenylsiloxanes, polydimethyldiphenylsiloxanes that are present in straight-chain and/or branched fashion and have at 25° C. a viscosity in the range from $1·10^{-5}$ to $5·10^{-2}$ m²/s;
(c) silicone rubbers are selected from among polydiorganosiloxanes that have number-average molar masses in the range from 200,000 to 1,000,000 and that are used as such or in a mixture with a solvent;
(d) resins are selected from among resins that are constructed from the units $R_3SiO_{1/2}$, $R_2SiO_{2/2}$, $RSiO_{3/2}$, and $SiO_{4/2}$, in which the group R signifies a hydrocarbon group having 1 to 16 carbon atoms or a phenyl group;
(e) organomodified silicones are selected from among silicones that carry in their structure one or more organofunctional groups which are bound via a hydrocarbon group.

Agents particularly preferred according to the present invention include the further silicone(s) preferably in quantities from 0.1 to 10 wt %, preferably from 0.25 to 7 wt %, and in particular from 0.5 to 5 wt %, based in each case on the total agent.

Preferred silicones are described below.

Particularly preferred agents according to the present invention are characterized in that they include at least one silicone of formula (Si—I)

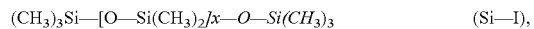

$(CH_3)_3Si—[O—Si(CH_3)_2]x—O—Si(CH_3)_3$ (Si—I), in which x denotes a number from 0 to 100, preferably from 0 to 50, more preferably from 0 to 20, and in particular 0 to 10.

These silicones are referred to according to INCI nomenclature as Dimethicones. The compounds recited in pages 28-29 of the priority document are preferably employed in the context of the present invention as a silicone of formula Si—I, wherein $(CH_3)_3Si—O—Si(CH_3)_3$, $(CH_3)_3Si—O—(CH_3)_2Si—O—Si(CH_3)_3$, and/or $(CH_3)_3Si—O—[O—(CH_3)_2Si]_2—O—Si(CH_3)_3$ are particularly preferred.

Mixtures of the silicones recited above can of course also be included in the agents according to the present invention.

Preferred silicones usable according to the present invention have viscosities from 0.2 to 2 mm²s⁻¹ at 20° C.; silicones having viscosities from 0.5 to 1 mm²s⁻¹ are particularly preferred.

Preferred cosmetic compositions according to the present invention are characterized in that the silicones, used individually or in a mixture, are selected from among the following structures:
  polydimethylsiloxane,
  polydimethylsiloxane/methylvinylsiloxanes,
  polydimethylsiloxane/diphenylsiloxane,
  polydimethylsiloxane/phenylmethylsiloxane,
  polydimethylsiloxane/diphenylsiloxane/methylvinylsiloxane, and the following mixtures:
  mixtures that are constituted from a polydimethylsiloxane hydroxylated at the chain end and a cyclic polydimethylsiloxane,
  mixtures that are constituted from a polydimethylsiloxane rubber and a cyclic silicone, and
  mixtures of polydimethylsiloxanes of different viscosities.

Particularly preferred agents according to the present invention include one or more organomodified silicones, since the applications-engineering properties of the silicones can be adapted to the intended application in even further detail by means of the modification. Cosmetic compositions preferred according to the present invention are characterized in that the organomodified silicones are selected from polyorganosiloxanes that include a) polyethyleneoxy and/or polypropyleneoxy groups,
b) substituted or unsubstituted aminated groups,
c) thiol groups,
d) alkoxylated groups,
e) hydroxyalkyl groups,
f) acyloxyalkyl groups,
g) carboxyalkyl groups,
h) 2-hydroxyalkylsulfonate groups,
i) 2-hydroxyalkylthiosulfonate groups,
j) hydroxyacylamino groups.

Particularly preferred agents according to the present invention include one or more aminofunctional silicones. Such silicones can be described, for example, by the formula

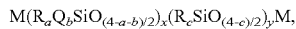

$M(R_aQ_bSiO_{(4-a-b)/2})_x(R_cSiO_{(4-c)/2})_yM$, wherein in the above formula, R is a hydrocarbon or a hydrocarbon residue having 1 to approximately 6 carbon atoms, Q is a polar residue of the general formula —$R^1HZ$, in which $R^1$ is a divalent connecting group that is bound to hydrogen and to the Z residue, assembled from carbon and hydrogen atoms, carbon, hydrogen, and oxygen atoms, or carbon, hydrogen, and nitrogen atoms, and Z is an organic aminofunctional residue that includes at least one aminofunctional group; "a" assumes values in the range from approximately 0 to approximately 2, "b" assumes values in the range from approximately 1 to approximately 3, "a"+"b" is less than or equal to 3, and "c" is a number in the range from approximately 1 to approximately 3, and x is a number in the range from 1 to approximately 2,000, preferably from approximately 3 to approximately 50, and most preferably from approximately 3 to approximately 25, and y is a number in the range from approximately 20 to approximately 10,000, preferably from approximately 125 to approximately 10,000, and most preferably from approximately 150 to approximately 1,000, and M is a suitable silicone terminal group as known in the existing art, preferably trimethylsiloxy. Non-limiting examples of the residues represented by R include alkyl residues such as methyl, ethyl, propyl, isopropyl, isopropyl, butyl, isobutyl, amyl, isoamyl, hexyl, isohexyl and the like; alkenyl residues such as vinyl, halovinyl, alkylvinyl, allyl, haloalkyl, alkylallyl; cycloalkyl residues such as cyclobutyl, cyclopentyl, cyclohexyl and the like; phenyl residues, benzyl residues, halogenated hydrocarbon residues such as 3-chloropropyl, 4-bromobutyl, 3,3,3-trifluoropropyl, chlorocyclohexyl, bromophenyl, chlorophenyl, and the like, as well as sulfur-containing residues such as mercaptoethyl, mercaptopropyl, mercaptohexyl, mercaptophenyl and the like; R is preferably an alkyl residue that includes 1 to approximately 6 carbon atoms, and R is most preferably methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, —$OCH_2CH_2$—, —$OCH_2CH_2CH_2$—, —$CH_2CH(CH_3)C(O)OCH_2$—, —$(CH_2)_3CC(O)OCH_2CH_2$—, —$C_6H_4C_6H_4$—, —$C_6H_4$—$CH_2C_6H_4$—, and —$(CH_2)_3C(O)SCH_2CH_2$—.

Z is an organic aminofunctional residue including at least one functional amino group. One possible formula for Z is $NH(CH_2)_zNH_2$, in which z is 1 or more. Another possible formula for Z is —$NH(CH_2)_z(CH_2)_{zz}NH$, in which both z and zz are independently 1 or more; this structure includes diamino ring structures such as piperazinyl. Z is most preferably a —$NHCH_2CH_2NH_2$ residue. Another possible formula for Z is —$N(CH_2)_z(CH_2)_{zz}NX_2$ or —$NX_2$, in which each X is selected, independently of $X_2$, from the group consisting of hydrogen and alkyl groups having 1 to 12 carbon atoms, and zz is 0.

Q is most preferably a polar aminofunctional residue of the formula —$CH_2CH_2CH_2NHCH_2CH_2NH_2$. In the formulas, "a" assumes values in the range from approximately 0 to approximately 2, "b" assumes values in the range from approximately 2 to approximately 3, "a"+"b" is less than or equal to 3, and "c" is a number in the range from approximately 1 to approximately 3. The molar ratio of the $R_aQ_bSiO_{(4-a-b)/2}$ units to the $R_cSiO_{(4-c)/2}$ units is in the range from approximately 1:2 to 1:65, preferably from approximately 1:5 to approximately 1:65, and most preferably from approximately 1:15 to approximately 1:20. If one or more silicones of the above formula are used, the different variable substituents in the above formula can then be different in the different silicone components that are present in the silicone mixture.

Preferred agents according to the present invention are characterized in that an aminofunctional silicone of formula (Si—II)

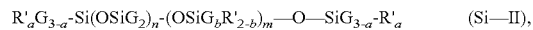

$R'_aG_{3-a}$-Si(OSiG$_2$)$_n$-(OSiG$_b$R'$_{2-b}$)$_m$—O—SiG$_{3-a}$-R'$_a$     (Si—II), is included, in which G is —H, a phenyl group, —OH, —O—$CH_3$, —$CH_3$, —O—$CH_2CH_3$, —$CH_2CH_3$, —O—$CH_2CH_2CH_3$, —$CH_2CH_2CH_3$, —O—$CH(CH_3)_2$, —$CH(CH_3)_2$, —O—$CH_2CH_2CH_2CH_3$, —$CH_2CH_2CH_2CH_3$, —O—$CH_2CH(CH_3)_2$, —$CH_2CH(CH_3)_2$, —O—$CH(CH_3)CH_2CH_3$, —$CH(CH_3)CH_2CH_3$, —O—$C(CH_3)_3$, —$C(CH_3)_3$;

a denotes a number between 0 and 3, in particular 0;

b denotes a number between 0 and 1, in particular 1, m and n are numbers whose sum (m+n) is between 1 and 2000, preferably between 50 and 150, wherein n preferably assumes values from 0 to 1999 and in particular from 49 to 149, and m preferably assumes values from 1 to 2000, in particular from 1 to 10;

R' is a monovalent residue selected from

-Q-N(R")—$CH_2$—$CH_2$—N(R")$_2$,

-Q-N(R")$_2$,

-Q-N$^+$(R")$_3$A$^-$,

-Q-N$^+$H(R")$_2$A$^-$,

-Q-N$^+$H$_2$(R")A$^-$,

-Q-N(R")—$CH_2$—$CH_2$–N$^+$R'H$_2$A$^-$, wherein each Q denotes a chemical bond, —$CH_2$—, —$CH_2$—$CH_2$—, —$CH_2CH_2CH_2$—, —$C(CH_3)_2$—, —$CH_2CH_2CH_2CH_2$—, —$CH_2C(CH_3)_2$—, —$CH(CH_3)CH_2CH_2$—, R" denotes identical or different residues from the group of —H, phenyl, benzyl, $CH_2$—$CH(CH_3)Ph$, $C_{1-20}$ alkyl residues, preferably —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, and A represents an anion that is preferably selected from chloride, bromide, iodide, or methosulfate.

Particularly preferred agents according to the present invention are characterized in that they include at least one aminofunctional silicone of formula (Si-IIa)

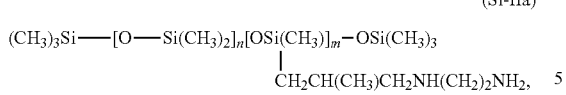

(Si-IIa)

$(CH_3)_3Si-[O-Si(CH_3)_2]_n[OSi(CH_3)]_m-OSi(CH_3)_3$
   |
   $CH_2CH(CH_3)CH_2NH(CH_2)_2NH_2$, in which m and n are numbers whose sum (m+n) is between 1 and 2000, preferably between 50 and 150, wherein n assumes values preferably from 0 to 1999 and in particular from 49 to 149, and m preferably assumes values from 1 to 2000, in particular from 1 to 10.

These silicones are referred to according to the INCI declaration as Trimethylsilylamodimethicones.

Also particularly preferred are agents according to the present invention that include an aminofunctional silicone of formula (Si-IIb)

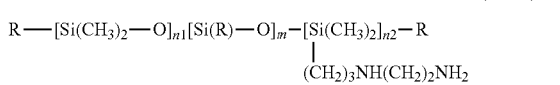

(Si-IIb)

$R-[Si(CH_3)_2-O]_{n1}[Si(R)-O]_m-[Si(CH_3)_2]_{n2}-R$
   |
   $(CH_2)_3NH(CH_2)_2NH_2$ in which R denotes —OH, —O—CH$_3$, or a —CH$_3$ group, and m, n1, and n2 are numbers whose sum (m+n1+n2) is between 1 and 2000, preferably between 50 and 150, wherein the sum (n1+n2) assumes values preferably from 0 to 1999 and in particular from 49 to 149, and m assumes values preferably from 1 to 2000, in particular from 1 to 10.

These silicones are referred to according to the INCI declaration as Amodimethicone.

Regardless of which aminofunctional silicones are employed, agents according to the present invention that include an aminofunctional silicone whose amine number is above 0.25 meq/g, preferably above 0.3 meq/g, and in particular above 0.4 meq/g, are preferred. The amine number denotes, in this context, the milliequivalent of amine per gram of aminofunctional silicone. It can be ascertained by titration, and also indicated using the unit of "mg KOH/g".

Agents preferred according to the present invention are characterized in that they include, based on their weight, 0.01 to 10 wt %, preferably 0.1 to 8 wt %, particularly preferably 0.25 to 7.5 wt %, and in particular 0.5 to 5 wt % aminofunctional silicone(s).

The cyclic dimethicones referred to according to INCI as Cyclomethicones are also usable with preference according to the present invention. Agents according to the present invention that include at least one silicone of formula Si-III

(Si-III)

$-[O-Si(CH_3)_2]_x-$ in which x denotes a number from 3 to 200, preferably from 3 to 10, more preferably from 3 to 7, and in particular 3, 4, 5, or 6, are preferred here.

Cyclic silicones having 3 to 7, preferably 4 to 5 silicon atoms are, for example, octamethylcyclotetrasiloxane, obtainable as "Volatile Silicone 7207" (Union Carbide) or "Silbione 70045 V 2" (Rhodia Chimie), decamethylcyclopentasiloxane, obtainable as "Volatile Silicone 7158" (Union Carbide) and "Silbione 70045 V 5" (Rhodia Chimie), and mixtures thereof.

Cyclopolymers of the dimethylsiloxane/methylalkylsiloxane type are, for example "Volatile Silicone FZ 3109" (Union Carbide), having the structure:

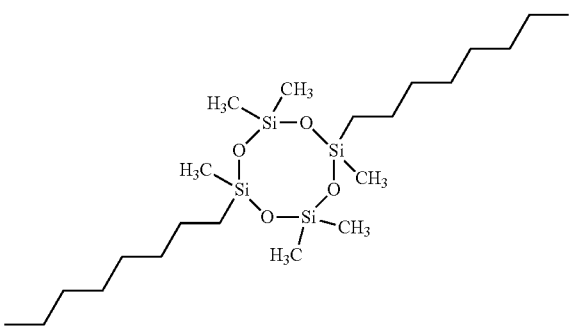 [SMILES: CCCCCCCC[Si]1(C)O[Si](C)(C)O[Si](C)(CCCCCCCC)O[Si](C)(C)O1]

Mixtures of cyclic silicones with organosilicone compounds can also be used, for example the mixture of octamethylcyclotetrasiloxane and tetratrimethylsilylpentaerythritol (50/50), and the mixture of octamethylcyclotetrasiloxane and oxy-1,1'-bis(2,2,2',2',3,3'-hexatrimethylsilyloxy)neopentane.

The silicones described above comprise a backbone that is constructed from —Si—O—Si— units. These —Si—O—Si— units can of course also be interrupted by carbon chains. Corresponding molecules are accessible via chain lengthening reactions, and are employed preferably in the form of silicone-in-water emulsions.

Agents likewise preferred according to the present invention are characterized in that they include at least one silicone of formula (Si-IV)

$R_3Si-[O-SiR_2]_x-(CH_2)_n-[O-SiR_2]_y-O-SiR_3$ (Si-IV), in which R denotes identical or different residues from the group —H, phenyl, benzyl, —CH$_2$—CH(CH$_3$)Ph, C$_{1-20}$ alkyl residues, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, x and y respectively denote a number from 0 to 200, preferably from 0 to 10, more preferably from 0 to 7, and in particular 0, 1, 2, 3, 4, 5, or 6, and n denotes a number from 0 to 10, preferably from 1 to 8, and in particular 2, 3, 4, 5, 6.

The silicones are preferably water-soluble. Agents preferred according to the present invention are characterized in that they include at least one water-soluble silicone.

Very particularly preferred cosmetic compositions are characterized in that the silicones are selected from polyalkylsiloxanes having terminal trimethylsilyl groups, polyalkylsiloxanes having terminal dimethylsilanol groups, polyalkylarylsiloxanes, mixtures of two PDMS that are constituted from a rubber and an oil of different viscosities, mixtures of organosiloxanes and cyclic silicones, organopolysiloxane resins.

Trade names of silicones preferably used as conditioning agents are, for example:
  decamethyltetrasiloxane "SH 200" (Toray Silicone)
  Silbione® oils of the 47 and 70 047 series
  Mirasil® oils (Rhodia Chimie) such as 70 047 V 500 000
  oils of the 200 series (Dow Corning), such as DC200 having a viscosity of 60 000 cSt (mm$^2$/s)
  Viscasil® oils (General Electric)
  oils of the SF Series (SF 96, SF 18, SF 1023, SF 1154, SF 1250, and SF 1265) of General Electric
  dimethiconols such as oils of the 48 series (Rhodia Chimie)
  Abil® Wax 9800 and 9801 (Goldschmidt)

Silbione oils of the 70 641 series (Rhodia Chimie)
oils of the Rhodorsil 70 633 and 763 series (Rhodia Chimie)
Dow Corning 556 Cosmetic Grade Fluid (Dow Corning)
Silicones of the PK series (Bayer), for example PK20
Silicones of the PN and PH series (Bayer), for example PN1000 and PH1000
Q2 1401 (Dow Corning)
SF 1214 Silicone Fluid (General Electric)
SF 1236 (General Electric)
"Dow Corning 593" or "Silicone Fluid SS 4230 and SS 4267" (General Electric)
X22-4914, X21-5034 and X21-5037 (Shin-Etsu)
DC 1248 and Q2 5200 (Dow Corning)
GP 4 Silicone Fluid and GP 7100 (Genesee)
Q2 8220 and Dow Corning 929 or 939 (Dow Corning)
GP 72 A and GP 71 (Genesee)
Silicone Copolymer F-755 (SWS Silicones) and Abil Wax 2428, 2434, and 2440 (Goldschmidt)
X-22-3701 E (Shin-Etsu)
Abil 5201 and Abil 5255 (Goldschmidt)
Q2-8413 (Dow Corning).

Water-soluble conditioning agents, preferably from the groups of anionic polymers, nonionic polymers, cationic polymers, amphoteric polymers, cationic proteins and protein hydrolysates, cationic surfactants, and mixtures of these substances, can also be used as conditioning agents.

The compositions according to the present invention can include polymers; particularly preferred in that context are the polymers disclosed on pages 36 to 44 of the priority document. Polymers are included in the agents according to the present invention preferably in quantities from 0.01 to 10 wt %, based on the total agent. Quantities from 0.1 to 5, in particular from 0.1 to 3 wt %, are particularly preferred.

Trade names of polymers preferably used as conditioning agents are, for example:
Versicol E or K (Ciba)
Ultrahold (BASF)
Reten 421, 423, or 425 (Hercules)
Quadramer (American Cyanamid)
Acrylidone LM (ISP)
Luvimer 100 P (BASF)
28-29-30, 26-13-14, and 28-13-10 (National Starch)
Gantrez AN or ES (ISP)
Flexan 500 and Flexan 130 (National Starch)
Cosmedia Polymer HSP 1 180 (Cognis)
Ultrahold Strong (BASF)
Resin 28-29-30 (National Starch)
Gantrez ES 425 (ISP)
Eudragit L (Rohm Phaana)
Luvimer MAEX or MAE (BASF)
Luviset CA 66 (BASF)
Aristoflex A (BASF)
Acrylidone LM (ISP)
Polyquart KE 3033 (Cognis)
Merquat 280, Merquat 295, and Merquat Plus 3330 (Nalco)
Diaformer Z301 (Sandoz)
N-carboxymethylchitosan and N-carboxybutylchitosan "Evalsan" (Jan Dekker)
Peox 50 000, Peox 200 000, and Peox 500 000
Appretan EM (Hoechst)
Rhodopas A 012 (Rhodia Chimie)
Rhodopas AD 310 (Rhodia Chimie)
Appretan TV (Hoechst)
Appretan MB Extra (Hoechst)
Micropearl RQ 750 (Matsumoto) and Luhydran A 848 S (BASF)
Primal AC-261 K and Eudragit NE 30 D/Rohm & Haas)
Acronal 601, Luhydran LR 8833 and 8845 (BASF)
Appretan N 9213 or N 9212 (Hoechst)
Nipol LX 531 B (Nippon Zeon)
CJ 0601 B (Rohm & Haas)
Acrysol RM 1020 and Acrysol RM 2020 (Rohm & Haas)
Uraflex XP 401 UZ and Uraflex XP 402 UZ (DSM Resins)
8538-33 (National Starch)
Estapor LO 11 (Rhodia Chimie)
Vidogum GH 175 (Unipectine)
Jaguar C (Meyhall)
Jaguar HP8, Jaguar HP60, and Jaguar HP120, Jaguar DC 293 and Jaguar HP 105
(Meyhall) Galactasol 4H4FD2 (Aqualon)
Hercofloc (Hercules)
Bina Quat P 100 (Ciba)
"Gafquat" (ISP), e.g. "Gafquat® 734" or "Gafquat® 755"
Copolymer 845, 958, and 937 (ISP)
Gaffix® VC 713 (ISP)
Styleze® CC 10 (ISP)
Gafquat® HS 100 (ISP)
(JR 400, JR 125, JR 30M) or (LR 400, LR 30M) (Amerchol)
Celquat® L 200 and Celquat® H 100 (National Starch)
Jaguar® C13S, Jaguar® C15, Jaguar® C17, and Jaguar® C162 (Meyhall)
Cartaretine® F, F4, or F8 (Sandoz)
PD 170 or Delsette® 101 (Hercules)
Mirapol® A 15, Mirapol® AD1, Mirapol® AZ1, and Mirapol® 175 (Miranol)
Luviquat® FC 905, FC 550, and FC 370 (BASF)
Polyquart® H (Cognis)
Salcare® SC 92 (Ciba)
Salcare® SC 95 and Salcare® SC 96 (Ciba)
Merquat® 100, Merquat® 550, and Merquat® S (Nalco)
Quat-Pro E (Maybrook)
Quat-Pro S (Maybrook)
Crotein® BTA, Croquat® L, Croquat® M, Croquat® S, Crotein® Q (Croda)
Lexein® QX 3000 (Inolex)
Hydrotriticum WQ or QM, Hydrotriticum QL, Hydrotriticum QS.

The agents according to the present invention can also include cationic surfactant(s), preferably in quantities from 0.1 to 20 wt %, as conditioning agents. Preferred cationic surfactants derive from the groups of quaternary ammonium compounds and/or esterquats and/or amidoamines.

Compounds of formula (Q-1)

(IV)

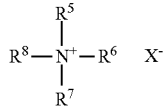

(Q-1)

in which at most three of the residues $R^5$ to $R^8$ mutually independently denote an alkyl group having 1 to 4 carbon atoms, at least one residue $R^5$ to $R^8$ denotes a saturated or unsaturated, branched or unbranched alkyl chain having 8 to 30 carbon atoms, and in which $X^-$ signifies a halide or a methosulfate group, have proven particularly suitable as quaternary ammonium compounds.

The short-chain alkyl group is particularly preferably a methyl group. Depending on how many long-chain alkyl groups are included in the molecule, formula (Q-1) denotes alkyltrimethylammonium halides and/or dialkyldimethylammonium halides and/or trialkylmethylammonium halides.

Preferred quaternary ammonium compounds of formula (Q-1) are ammonium halides, in particular chlorides and bromides, such as alkyltrimethylammonium chlorides, dialkyldimethylammonium chlorides, and trialkylmethylammonium chlorides, e.g. distearyldimethylammonium chloride, lauryltrimethylammonium chloride, lauryltrimethylbenzylammonium chloride, tricetylmethylammonium chloride, cetyltrimethylammonium chloride, cetyltrimethylammonium bromide, cetyltrimethylammonium methosulfate, stearyltrimethylammonium chloride, behenyltrimethylammonium chloride, behenyltrimethylammonium bromide, and behenyltrimethylammonium methosulfate. Cetyltrimethylammonium salts and behenyltrimethylammonium salts are preferred.

Cetyltrimethylammonium salts are particularly preferred, in particular cetyltrimethylammonium chloride and/or cetyltrimethylammonium methosulfate.

In summary, preferred cosmetic compositions according to the present invention are characterized in that they include 0.15 to 15 wt %, preferably 0.2 to 10 wt %, more preferably 0.25 to 7.5 wt %, even more preferably 0.5 to 5 wt %, and in particular 0.75 to 2.5 wt % quaternary ammonium compounds from the groups of
  i. alkyltrimethylammonium chlorides, and/or
  ii. dialkyldimethylammonium chlorides, and/or
  iii. trialkylmethylammonium chlorides.

Very particularly preferred cosmetic compositions according to the present invention are characterized in that they include 0.15 to 15 wt %, preferably 0.2 to 10 wt %, more preferably 0.25 to 7.5 wt %, even more preferably 0.5 to 5 wt %, and in particular 0.75 to 2.5 wt % cetyltrimethylammonium chloride.

Quaternary imidazoline compounds, i.e. compounds that comprise a positively charged imidazoline ring, can also be employed as quaternary ammonium compounds. Formula (Q-2) depicted below shows the structure of these compounds.

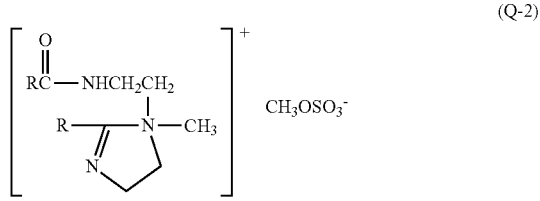

(Q-2)

The residues R mutually independently each denote a saturated or unsaturated, linear or branched hydrocarbon residue having a chain length from 8 to 30 carbon atoms. The preferred compounds of formula I include the same hydrocarbon residue for each R. The chain length of the residues R is preferably 12 carbon atoms. Compounds having a chain length of at least 16 carbon atoms are particularly preferred, and those having at least 20 carbon atoms are very particularly preferred. A very particularly preferred compound of formula (Q-2) has a chain length of 21 carbon atoms. A commercial product of this chain length is known, for example, by the name Quatemium-91. Methosulfate is depicted in formula (Q-2) as a counter ion. Also comprised according to the present invention as counter ions, however, are the halides such as chloride, fluoride, bromide, or also phosphates.

The imidazolines of formula (Q-2) are included in the compositions according to the present invention by preference in quantities from 0.01 to 20 wt %, preferably in quantities from 0.05 to 10 wt %, and very particularly preferably in quantities from 0.1 to 7.5 wt %. The best results of all are obtained with quantities from 0.1 to 5 wt %, based in each case on the total composition of the respective agent.

Compounds selected from the group of
  quaternized ester salts of fatty acids with triethanolamine (so-called "esterquats"), in particular the salts of N,N-di(2-(dodecanoyloxy)ethyl)dimethylammonium, N,N-di(2-(tetradecanoyloxy)ethyl)dimethylammonium, N,N-di(2-(hexadecanoyloxy)ethyl)dimethylammonium, N,N-di(2-(hexadecanoyloxy)propyl)dimethylammonium, N,N-di(2-(octadecanoyloxy)ethyl)dimethylammonium with a physiologically acceptable organic or inorganic anion. Preferred anions are alkyl sulfates, for example methyl sulfate, and halides, such as chloride and bromide. Products of this kind are marketed, for example, under the trademarks Stepantex, Dehyquart®, and Armocare®. The products Armocare® VGH-70, an N,N-di(2-hexadecanoyloxyethyl)dimethylammonium chloride, and Dehyquart® L80 (INCI name: Dicocoylethyl Hydroxyethylmonium Methosulfate), Dehyquart® F-75, Dehyquart® C-4046, and Dehyquart® AU-35 are examples of such esterquats. Fatty acid cuts, e.g. tallow fatty acids recovered from tallow, for example beef tallow, can also be used for manufacture (INCI names: Ditallowoylethyl Dimonium Methosulfate, Ditallowoyl PG-Dimonium Chloride),
  salts of N,N-dimethyl-N-(2-hydroxyethyl)-N-(2-hydroxyhexadecyl)ammonium. Preferred halides are chloride and bromide. These are marketed, for example under the trademark Dehyquart® E (INCI name: Aqua (Water), Hydroxycetyl Hydroxyethyl Dimonium Chloride) by the Cognis company,
  quaternized amide salts of fatty acids with diamines, for example salts of N-(13-docosen)amidopropyl-N-2-hydroxyethyl-N,N-dimethylammonium (INCI name: Hydroxyethyl Erucamidopropyl Dimonium Chloride) or of N-docosylamidopropyl-N-2-hydroxyethyl-N,N-dimethylammonium, which is marketed under the commercial name Incroquat® Behenyl HE (INCI name: Hydroxyethyl Behenamidopropyl Dimonium Chloride) by Croda Inc.
can also be used as quaternary ammonium compounds.

Cosmetic compositions preferred according to the present invention are characterized in that they include 0.15 to 15 wt %, preferably 0.2 to 10 wt %, more preferably 0.25 to 7.5 wt %, even more preferably 0.5 to 5 wt %, and in particular 0.75 to 2.5 wt % of at least one esterquat from the groups of
  iv. quaternized ester salts of fatty acids with triethanolamine, and/or
  v. quaternized ester salts of fatty acids with diethanolalkylamines, and/or
  vi. quaternized ester salts of fatty acids with 1,2-dihydroxypropyldialkylamines.

Very particularly preferred cosmetic compositions according to the present invention are characterized in that they include 0.15 to 15 wt %, preferably 0.2 to 10 wt %, more preferably 0.25 to 7.5 wt %, even more preferably 0.5 to 5 wt %, and in particular 0.75 to 2.5 wt % distearoylethylhydroxyethylammonium methosulfate.

Particularly preferred quaternary ammonium compounds can be described by the formula (Q-3)

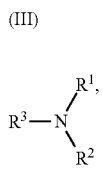

(III)

(Q-3)

and include methyl groups as residues $R^1$ and $R^2$, an $R^4$—CO(NH)—$(CH_2)_n$ groups as residue $R^3$, a saturated or unsaturated, branched or unbranched alkyl chain having 11 to 19 carbon atoms as residue $R^4$, and in which n signifies the number 3. Such compounds are known by the name "amidoamine."

Amidoamines can be present in the cosmetic compositions both as such, and (as a consequence of protonation in a correspondingly acidic solution) as a corresponding quaternary compound thereof.

Non-cationic amidoamines are preferred according to the present invention.

Suitable amidoamines, which optionally can be quaternized, are: Tego Amid® S18 (Evonik; INCI name: Stearamidopropyl Dimethylamine), Lexamine® S 13 (Inolex; INCI name: Stearamidopropyl Dimethylamine), Incromine® SB (Croda; INCI name: Stearamidopropyl Dimethylamine), Witcamine® 100 (Witco, INCI name: Cocamidopropyl Dimethylamine), Incromine® BB (Croda, INCI name: Behenamidopropyl Dimethylamine), Mackine® 401 (McIntyre, INCI name: Iso stearylamidopropyl Dimethylamine) and other Mackine grades, Adogen® S18V (Witco, INCI name: Stearylamidopropyl Dimethylamine). Suitable permanently cationic ones are: Aminoamine: Rewoquat® RTM 50 (Witco Surfactants GmbH, INCI name: Ricinoleamidopropyltrimonium Methosulfate), Empigen® CSC (Albright & Wilson, INCI name: Cocamidopropyltrimonium Chloride), Swanol Lanoquat® DES-50 (Nikko, INCI name: Quaternium-33), Rewoquat® UTM 50 (Witco Surfactants GmbH, Undecyleneamidopropyltrimonium Methosulfate).

Stearamidopropyl Dimethylamine is particularly preferred.

Cosmetic compositions preferred according to the present invention are characterized in that the cationic surface-active substances are selected from:
(A) quaternary ammonium salts of the following general formula (XXIII):

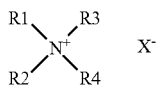

(XXIII)

in which X is an anion that is selected from among halides, alkyl ($C_{2-6}$) sulfates, phosphates, alkyl- or alkylarylsulfonates, and anions derived from an organic acid, and
i) the groups $R_1$ to $R_3$, which can be identical or different, signify a straight-chain or branched aliphatic group having 1 to 4 carbon atoms or an aromatic group, wherein the aliphatic groups can include heteroatoms; the group $R_4$ is a straight-chain or branched alkyl group having 16 to 30 carbon atoms;
ii) the groups $R_1$ and $R_2$, which can be identical or different, signify a straight-chain or branched aliphatic group having 1 to 4 carbon atoms or an aromatic group, wherein the aliphatic groups can include heteroatoms;
the groups $R_3$ and $R_4$, which can be identical or different, signify a straight-chain or branched alkyl group having 12 to 30 carbon atoms, wherein the group comprises at least one ester function or amide function;
(B) quaternary ammonium salts of imidazolinium;
(C) quaternary diammonium salts of formula (XXV):

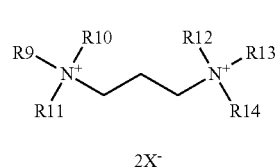

(XXV)

$2X^-$ in which the group $R_9$ signifies an aliphatic group having approximately 16 to 30 carbon atoms, the groups $R_{10}$, $R_{11}$, $R_{12}$, $R_{13}$, and $R_{14}$, which can be identical or different, are selected from among hydrogen or an alkyl group having 1 to 4 carbon atoms, and X is an anion that is selected from among halides, acetates, phosphates, nitrates, and methyl sulfates;
(D) quaternary ammonium salts that include at least one ester function of the following formula (XXVI);

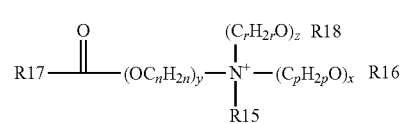

(XXVI)

in the formula:
$R_{15}$ is selected from among $C_{1-6}$ alkyl groups and hydroxyalkyl or dihydroxyalkyl groups having 1 to 6 carbon atoms;
$R_{16}$ is selected from among:
a group R19-C(O)—
hydrocarbon-based groups $R_{20}$ having 1 to 22 carbon atoms, which can be straight-chain or branched, saturated or unsaturated, a hydrogen atom,
$R_{18}$ is selected from among:
a group R21-C(O)—
hydrocarbon-based groups $R_{22}$ having 1 to 6 carbon atoms, which can be straight-chain or branched, saturated or unsaturated,
a hydrogen atom,
$R_{17}$, $R_{19}$, and $R_{21}$, which can be identical or different from one another, are selected from among straight-chain or branched, saturated or unsaturated $C_{7-21}$ hydrocarbon groups;
n, p, and r, which can be identical or different, are integers from 2 to 6;
y is an integer in the range from 1 to 10;
x and z, which can be identical or different, signify 0 or an integer from 1 to 10;
$X^-$ is a simple or complex, organic or inorganic anion; with the provision that the sum x+y+z is in the range from 1 to 15, that $R_{16}$ signifies $R_{20}$ when x is 0, and that $R_{18}$ signifies $R_{22}$ when z is 0.
Regardless of the conditioning agent(s) selected, cosmetic compositions according to the present invention that include the conditioning agent(s) in a total quantity from 0.001 to 20 wt %, preferably from 0.01 to 15 wt %, more preferably from 0.1 to 10 wt %, and in particular from 0.25 to 5 wt %, based on the total weight of the composition, are preferred.

Depending on the intended use, the agents according to the present invention include further essential ingredients. Cleaning or care-providing compositions such as shampoos or conditioners include at least one surfactant, wherein surface-active substances are referred to as "surfactants" or as "emulsifier agents" depending on the area of use, and are selected from anionic, cationic, zwitterionic, ampholytic, and nonionic surfactants and emulsifier agents.

Cosmetic agents preferred according to the present invention are characterized in that they include, based on their weight, 0.5 to 70 wt %, preferably 1 to 60 wt %, and in particular 5 to 25 wt % anionic and/or nonionic and/or cationic and/or amphoteric surfactant(s). Surfactants from the aforementioned groups to be used particularly preferably according to the present invention are disclosed in detail on pages 46 to 62 of the priority document.

The care-providing effects of the agents according to the present invention can be even further intensified by employing specific care-providing substances. The latter are preferably selected from specific groups of care-providing substances known per se, since these care-providing substances harmonize outstandingly in terms of formulation engineering and care-providing effect with the 4-morpholinomethyl-substituted silicones used according to the present invention.

Cosmetic agents preferred according to the present invention are characterized in that they additionally include, based on their weight, care-providing substances in quantities from 0.001 to 10 wt %, preferably 0.005 to 7.5 wt %, particularly preferably 0.01 to 5 wt %, and in particular 0.05 to 2.5 wt %, wherein preferred care-providing substance(s) are selected from the group:
i. L-carnitine and/or salts thereof;
ii. panthenol and/or pantothenic acid;
iii. 2-furanone and/or derivatives thereof, in particular pantolactone;
iv. taurine and/or salts thereof;
v. niacinamide;
vi. ubiquinone;
vii. ectoin;
viii. allantoin.

In hair treatment agents according to the present invention of this embodiment, the 4-morpholinomethyl-substituted silicones are combined with at least one care-providing substance that is selected from L-carnitine and/or salts thereof, panthenol and/or pantothenic acid, 2-furanones and/or derivatives thereof, in particular pantolactone, taurine and/or salts thereof, niacinamide, ubiquinones, ectoin, allantoin. These care-providing substances are described below.

L-Carnitine (IUPAC name (R)-(3-carboxy-2-hydroxypropyl)-N,N,N-trimethylammonium hydroxide) is a naturally occurring vitamin-like substance. As a betaine, L-carnitine can form addition compounds and double salts. L-Carnitine derivatives preferred according to the present invention are selected in particular from acetyl-L-carnitine, L-carnitine fumarate, L-carnitine citrate, lauroyl-L-carnitine, and particularly preferably L-carnitine tartrate. The aforesaid L-carnitine compounds are obtainable, for example, from Lonza GmbH (Wuppertal, Germany).

Preferred cosmetic agents according to the present invention are characterized in that they include, based on their weight, 0.001 to 10 wt %, preferably 0.005 to 7.5 wt %, particularly preferably 0.01 to 5 wt %, and in particular 0.05 to 2.5 wt % L-carnitine or L-carnitine derivatives, wherein preferred L-carnitine derivatives are selected from acetyl-L-carnitine, L-carnitine fumarate, L-carnitine citrate, lauroyl-L-carnitine, and in particular L-carnitine tartrate.

Panthenol (IUPAC-Name: (+)-(R)-2,4-dihydroxy-N-(3-hydroxypropyl)-3,3-dimethylbutyramide) is converted in the body to pantothenic acid. Pantothenic acid is a vitamin from the group of the B vitamins (vitamin B5).

Preferred cosmetic agents according to the present invention are characterized in that they include, based on its weight, 0.01 to 5 wt %, preferably 0.05 to 2.5 wt %, particularly preferably 0.1 to 1.5 wt %, and in particular 0.25 to 1 wt % panthenol ((±)-2,4-dihydroxy-N-(3-hydroxypropyl)-3,3-dimethylbutyramide).

Cosmetic agents preferred according to the present invention include, based on their weight, 0.01 to 15 wt %, preferably 0.025 to 12.5 wt %, particularly preferably 0.05 to 10 wt %, more preferably 0.1 to 7.5 wt %, and in particular 0.5 to 5 wt % of at least one 2-furanone derivative of formula (Fur-I) and/or of formula (Fur-II)

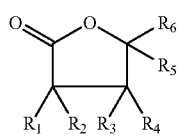

(Fur-I)

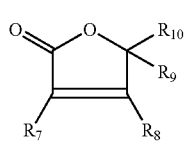

(Fur-II)

in which the residues $R^1$ to $R^{10}$ mutually independently denote:
hydrogen, —OH, a methyl, methoxy, aminomethyl, or hydroxymethyl residue,
a $C_2$ to $C_4$ saturated or mono- or diunsaturated, branched or linear hydrocarbon residue,
a $C_2$ to $C_4$ saturated or mono- or diunsaturated, branched or linear mono-, di- or trihydroxy hydrocarbon residue,
a $C_2$ to $C_4$ saturated or mono- or diunsaturated, branched or linear mono-, di- or triamino hydrocarbon residue,
an —$OR^{11}$ group, having $R^{11}$ as a $C_2$ to $C_4$ saturated or mono- or diunsaturated, branched or linear hydrocarbon residue, a $C_2$ to $C_4$ saturated or mono- or diunsaturated, branched or linear mono-, di- or trihydroxy hydrocarbon residue,
an —$NR^{12}R^{13}$ group, wherein $R^{12}$ and $R^{13}$ each mutually independently denote hydrogen, a methyl residue, a $C_2$ to $C_4$ saturated or mono- or diunsaturated, branched or linear hydrocarbon residue, a $C_2$ to $C_4$ saturated or mono- or diunsaturated, branched or linear mono-, di- or trihydroxy hydrocarbon residue,
a —$COOR^{14}$ group, wherein $R^{14}$ denotes hydrogen, a methyl residue, a $C_2$ to $C_4$ saturated or mono- or diunsaturated, branched or linear hydrocarbon residue, a $C_2$ to $C_4$ saturated mono- or diunsaturated, branched or linear mono-, di- or trihydroxy hydrocarbon residue, a $C_2$ to $C_4$ saturated or mono- or diunsaturated, branched or linear mono-, di- or triamino hydrocarbon residue,
a —$CONR^{15}R^{16}$ group, wherein $R^{15}$ and $R^{16}$ each denote hydrogen, methyl, a $C_2$ to $C_4$ saturated or mono- or diunsaturated, branched or linear hydrocarbon residue, a $C_2$ to $C_4$ saturated mono- or diunsaturated, branched or linear mono-, di- or trihydroxy hydrocarbon residue, a $C_2$ to $C_4$ saturated or mono- or diunsaturated, branched or linear mono-, di- or triamino hydrocarbon residue, a —$COR^{16}$ group, wherein $R^{16}$ denotes a methyl residue, a $C_2$ to $C_4$ saturated or mono- or diunsaturated, branched or linear hydrocarbon residue, a $C_2$ to $C_4$ saturated or mono- or diunsaturated, branched or linear mono-, di- or trihydroxy hydrocarbon residue, a $C_2$ to $C_4$ saturated or mono- or diunsaturated, branched or linear mono-, di- or triamino hydrocarbon residue, an —$OCOR^{17}$ group, wherein $R^{17}$ denotes a methyl residue, a $C_2$ to $C_{30}$ saturated or mono- or polyunsaturated, branched or linear hydrocarbon residue, a $C_2$ to $C_{30}$ saturated or mono- or polyunsaturated, branched or linear mono-, di-, tri-, or polyhydroxy hydrocarbon residue, a $C_2$ to $C_{30}$ saturated or mono- or polyunsaturated, branched or linear mono, di-, tri-, or polyamino hydrocarbon residue, with the provision that for the case in which $R^7$ and $R^8$ denote —OH and $R^9$ or $R^{19}$ simultaneously denotes hydrogen, the remaining group $R^9$ or $R^{10}$ does not denote a dihydroxyethyl residue.

The compounds of formulas (Fur-I) and (Fur-II) are employed as intermediates in natural-substance synthesis and the manufacture of pharmaceuticals and vitamins. The active agents in accordance with formulas (Fur-I) and (Fur-II) can be manufactured, for example, by reacting primary alcohols with acrylic acids. Compounds of formula (Fur-I) are furthermore arrived at by way of reactions proceeding from hydroxypivaldehyde. Carbonylations of alkynes likewise lead to substituted 2-furanones of formula (Fur-I) or (Fur-II). Lastly, the compounds of formula (Fur-I) or formula (Fur-II) can be obtained by intramolecular esterification of the corresponding hydroxycarboxylic acids.

For example, the following compounds are obtained by one of the synthesis paths presented above: 2,5-dihydro-5-methoxy-2-furanone, tetrahydro-5-oxo-2-furancarboxylic acid, dihydro-3-hydroxy-4,4-dimethyl-2(3H)-furanone, or 3,4-dimethyl-5-pentylidenedihydro-2(5H)-furanone or 4-hydroxy-2,5-dimethyl-3(2H)-furanone. The 2-furanones according to the present invention of course comprise all possible stereoisomers as well as mixtures thereof. The odor of the cosmetic agents is not lastingly influenced by the 2-furanones according to the present invention, so that perfuming of the agents must occur separately.

Preferred compounds of formula (Fur-I) and/or formula (Fur-II) can be compounds in which the substituents $R^1$, $R^2$, and $R^7$ mutually independently denote:
hydrogen, an —OH, methyl, methoxy, aminomethyl, hydroxymethyl residue,
a $C_2$ to $C_4$ saturated or mono- or diunsaturated, branched or linear mono-, di- or trihydroxy hydrocarbon residue,
a $C_2$ to $C_4$ saturated or mono- or diunsaturated, branched or linear mono-, di- or triamino hydrocarbon residue,
an —$OR^{11}$ group, having $R^{11}$ as a $C_2$ to $C_4$ saturated or mono- or diunsaturated, branched or linear hydrocarbon residue, a $C_2$ to $C_4$ saturated or mono- or diunsaturated, branched or linear mono-, di- or trihydroxy hydrocarbon residue,
an —$NR^{12}R^{13}$ group, wherein $R^{12}$ and $R^{13}$ each mutually independently denote hydrogen, a methyl residue, a $C_2$ to $C_4$ saturated or mono- or diunsaturated, branched or linear hydrocarbon residue, a $C_2$ to $C_4$ saturated or mono- or diunsaturated, branched or linear mono-, di- or trihydroxy hydrocarbon residue,
a —$COOR^{14}$ group, wherein $R^{14}$ denotes hydrogen, a methyl residue, a $C_2$ to $C_4$ saturated or mono- or diunsaturated, branched or linear hydrocarbon residue, a $C_2$ to $C_4$ saturated or mono- or diunsaturated, branched or linear mono-, di- or trihydroxy hydrocarbon residue, a $C_2$ to $C_4$ saturated or mono- or diunsaturated, branched or linear mono-, di- or triamino hydrocarbon residue,
a —$COR^{16}$ group, wherein $R^{16}$ denotes a methyl residue, a $C_2$ to $C_4$ saturated or mono- or diunsaturated, branched or linear hydrocarbon residue, a $C_2$ to $C_4$ saturated or mono- or diunsaturated, branched or linear mono-, di- or trihydroxy hydrocarbon residue, a $C_2$ to $C_4$ saturated or mono- or diunsaturated, branched or linear mono-, di- or triamino hydrocarbon residue,
an —$OCOR^{17}$ group, wherein $R^{17}$ denotes a methyl residue, a $C_2$ to $C_{30}$ saturated or mono- or polyunsaturated, branched or linear hydrocarbon residue, a $C_2$ to $C_{30}$ saturated or mono- or polyunsaturated, branched or linear mono-, di-, tri-, or polyhydroxyalkyl residue, or a $C_2$ to $C_{30}$ saturated or mono- or polyunsaturated, branched or linear mono, di-, tri-, or polyamino hydrocarbon residue.

In a further embodiment of the teaching according to the present invention, it has been found that in the context of the compounds of formula (Fur-I) or formula (Fur-II), the residues $R^3$, $R^4$, and $R^5$ preferably mutually independently denote:
hydrogen, an —OH, methyl, methoxy, aminomethyl, hydroxymethyl residue,
a $C_2$ to $C_4$ saturated or mono- or diunsaturated, branched or linear hydrocarbon residue,
a $C_2$ to $C_4$ saturated or mono- or diunsaturated, branched or linear mono-, di- or trihydroxy hydrocarbon residue,
a $C_2$ to $C_4$ saturated or mono- or diunsaturated, branched or linear mono-, di- or triamino hydrocarbon residue.

It can furthermore be preferred if, in the active agent according to the present invention in accordance with formula (I) and/or formula (II), the residues $R^5$, $R^6$, $R^9$, and $R^{10}$ mutually independently denote:
hydrogen, an —OH, methyl, methoxy, aminomethyl, hydroxymethyl residue,
a $C_2$ to $C_4$ saturated or mono- or diunsaturated, branched or linear hydrocarbon residue,
a $C_2$ to $C_4$ saturated or mono- or diunsaturated, branched or linear mono-, di- or trihydroxy hydrocarbon residue,
a $C_2$ to $C_4$ saturated or mono- or diunsaturated, branched or linear mono-, di- or triamino hydrocarbon residue.

In a particularly preferred embodiment of the teaching according to the present invention, a compound of formula (Fur-I) is employed. It can be preferred in this context that, in a compound of formula (Fur-I), the residues $R^1$ and $R^2$ mutually independently denote:
hydrogen, an —OH, methyl, methoxy, aminomethyl, hydroxymethyl residue,
a $C_2$ to $C_4$ saturated or mono- or diunsaturated, branched or linear mono-, di- or trihydroxy hydrocarbon residue,
an —$OR^{11}$ group, having $R^{11}$ as a $C_2$ to $C_4$ saturated or mono- or diunsaturated, branched or linear hydrocarbon residue, a $C_2$ to $C_4$ saturated or mono- or diunsaturated, branched or linear mono-, di- or trihydroxy hydrocarbon residue,
a —$COOR^{14}$ group, wherein $R^{14}$ denotes hydrogen, a methyl residue, a $C_2$ to $C_4$ saturated or mono- or diunsaturated, branched or linear hydrocarbon residue, a $C_2$ to $C_4$ saturated mono- or diunsaturated, branched or linear mono-, di- or trihydroxy hydrocarbon residue, a —COR$^{16}$ group, wherein R$^{16}$ denotes a methyl residue, a C$_2$ to C$_4$ saturated or mono- or diunsaturated, branched or linear hydrocarbon residue, a C$_2$ to C$_4$ saturated or mono- or diunsaturated, branched or linear mono-, di- or trihydroxy hydrocarbon residue, an —OCOR$^{17}$ group, wherein R$^{17}$ denotes a methyl residue, a C$_2$ to C$_{30}$ saturated or mono- or polyunsaturated, branched or linear hydrocarbon residue, a C$_2$ to C$_{30}$ saturated or mono- or polyunsaturated, branched or linear mono-, di-, tri-, or polyhydroxy hydrocarbon residue.

It can furthermore be advantageous in this particularly preferred embodiment of the teaching according to the present invention if, in the compounds of formula (Fur-I), the residues R$^3$ and R$^4$ mutually independently denote:

hydrogen, an —OH, methyl, methoxy, aminomethyl, hydroxymethyl residue, a C$_2$ to C$_4$ saturated or mono- or diunsaturated, branched or linear mono-, di- or trihydroxy hydrocarbon residue, an —OR$^{11}$ group, having R$^{11}$ as a C$_2$ to C$_4$ saturated or mono- or diunsaturated, branched or linear hydrocarbon residue, a C$_2$ to C$_4$ saturated or mono- or diunsaturated, branched or linear mono-, di- or trihydroxy hydrocarbon residue, a —COOR$^{14}$ group, wherein R$^{14}$ denotes hydrogen, a methyl residue, a C$_2$ to C$_4$ saturated or mono- or diunsaturated, branched or linear hydrocarbon residue, a C$_2$ to C$_4$ saturated mono- or diunsaturated, branched or linear mono-, di- or trihydroxy hydrocarbon residue, an —OCOR$^{17}$ group, wherein R$^{17}$ denotes a methyl residue, a C$_2$ to C$_{30}$ saturated or mono- or polyunsaturated, branched or linear hydrocarbon residue, a C$_2$ to C$_{30}$ saturated or mono- or polyunsaturated, branched or linear mono-, di-, tri-, or polyhydroxy hydrocarbon residue.

In this preferred embodiment it can furthermore be advantageous that in the compounds in accordance with formula (Fur-I), the residues R$^5$ and R$^6$ mutually independent denote:

a C$_2$ to C$_4$ saturated or mono- or diunsaturated, branched or linear mono-, di- or trihydroxy hydrocarbon residue, an —OR$^{11}$ group, having R$^{11}$ as a C$_2$ to C$_4$ saturated or mono- or diunsaturated, branched or linear hydrocarbon residue, a C$_2$ to C$_4$ saturated or mono- or diunsaturated, branched or linear mono-, di- or trihydroxy hydrocarbon residue.

In a particularly preferred embodiment of the teaching according to the present invention,
(R)-(−)-4-hydroxymethyl-γ-butyrolactone and/or
D,L-4-hydroxymethyl-γ-butyrolactone and/or
(S)-(+)-4-hydroxymethyl-γ-butyrolactone and/or
R-(+2-hydroxy-3,3-dimethyl-γ-butyrolactone and/or
D,L-2-hydroxy-3,3-dimethyl-γ-butyrolactone and/or
S(+)-2-hydroxy-3,3-dimethyl-γ-butyrolactone and/or
4-hydroxy-2,5-dimethyl-3(2H)-furanone and/or
tetrahydro-5-oxo-2-furancarboxylic acid and/or
tetrahydro-5-oxo-2-furancarboxylic acid, sodium salt and/or
tetrahydro-5-oxo-2-furancarboxylic acid, potassium salt and/or
2,5-dihydro-5-methoxy-2-furanone and/or
dihydro-3-hydroxy-4,4-dimethyl-2(3H)-furanone
are used as a compound corresponding to formula (Fur-I). In a very particularly preferred embodiment of the teaching according to the present invention, dihydro-3-hydroxy-4,4-dimethyl-2(3H)-furanone is used as a compound corresponding to formula (Fur-I).

A further care-providing substance preferred for use, which possesses activating properties, is taurine. Cosmetic agents preferred according to the present invention include, based on their weight, 0.01 to 15 wt %, preferably 0.025 to 12.5 wt %, particularly preferably 0.05 to 10 wt %, more preferably 0.1 to 7.5 wt %, and in particular 0.5 to 5 wt % taurine (2-aminoethanesulfonic acid).

A further preferred group of care-providing substances in the agents according to the present invention are vitamins, provitamins, or vitamin precursors. These are described below:

The group of substances referred to as "vitamin A" includes retinol (vitamin A$_1$) as well as 3,4-didehydroretinol (vitamin A$_2$). β-Carotene is the provitamin of retinol. Vitamin A components that are suitable according to the present invention are, for example, vitamin A acid and esters thereof, vitamin A aldehyde, and vitamin A alcohol, as well as esters thereof such as the palmitate and acetate. The agents according to the present invention include the vitamin A component preferably in quantities from 0.05 to 1 wt %, based on the total preparation.

Members of the vitamin B group or vitamin B complex are, among others:

Vitamin B$_1$ (thiamine)

Vitamin B2 (riboflavin)

Vitamin B$_3$. The compounds nicotinic acid and nicotinic acid amide (niacinamide) are often listed under this designation. Nicotinic acid amide is preferred according to the present invention; it is included in the agents used according to the present invention preferably in quantities from 0.05 to 1 wt % based on the total agent.

Vitamin B$_5$ (pantothenic acid, panthenol, and pantolactone). In the context of this group, panthenol and/or pantolactone are preferably used (see below). Derivatives of panthenol that are usable according to the present invention are in particular esters and ethers of panthenol, and cationically derivatized panthenols. Individual representatives are, for example, panthenol triacetate, panthenol monoethyl ether and the monoacetate thereof, and the cationic panthenol derivatives disclosed in WO 92/13829. The aforesaid compounds of the vitamin Bs type are included in the agents according to the present invention preferably in quantities from 0.05 to 10 wt % based on the total agent. Quantities from 0.1 to 5 wt % are particularly preferred.

Vitamin B6 (pyridoxine as well as pyridoxamine and pyridoxal).

Vitamin C (ascorbic acid). Vitamin C is employed in the agents according to the present invention preferably in quantities from 0.1 to 3 wt % based on the total agent. Utilization in the form of the palmitic acid ester, glucosides, or phosphates can be preferred. Utilization in combination with tocopherols can likewise be preferred.

Vitamin E (tocopherols, in particular α-tocopherol). Tocopherol and its derivatives, which include in particular esters such as the acetate, nicotinate, phosphate, and succinate, are included in the agents according to the present invention preferably in quantities from 0.05 to 1 wt % based on the total agent.

Vitamin F. The term "vitamin F" is usually understood to mean essential fatty acids, in particular linoleic acid, linolenic acid, and arachidonic acid.

Vitamin H. "Vitamin H" refers to the compound (3aS,4S,6aR)-2-oxohexahydrothienol[3,4-d]-imidazole-4-valeric acid, for which the trivial name "biotin" has, however, now become established. Biotin is included in the agents according to the present invention preferably in quantities from 0.0001 to 1.0 wt %, in particular in quantities from 0.001 to 0.01 wt %.

In summary, those cosmetic agents according to the present invention which include, based on their weight, 0.1 to 5 wt %, preferably 0.2 to 4 wt %, particularly preferably 0.25 to 3.5 wt %, more preferably 0.5 to 3 wt %, and in particular 0.5 to 2.5 wt % vitamins and/or provitamins and/or vitamin precursors that are allocated preferably to the groups A, B, C, E, F, and H, are preferred; preferred agents include -(2,4-dihydroxy-N-(3-hydroxypropyl)-3,3-dimethylbutyramide, (provitamin $B_5$) and/or panthothenic acid (vitamin $B_3$, vitamin $B_5$) and/or niacin, niacinamide or nicotinamide (vitamin $B_3$) and/or L-ascorbic acid (vitamin C) and/or thiamine (vitamin $B_1$) and/or riboflavin (vitamin $B_2$, vitamin G) and/or biotin (vitamin $B_7$, vitamin H) and/or folic acid (vitamin $B_9$, vitamin $B_c$ or vitamin M) and/or vitamin $B_6$ and/or vitamin $B_{12}$.

It has been found that specific quinones have a particular suitability as a care-providing substance. The agents according to the present invention can therefore include, as a further care-providing substance, 0.0001 to 5 wt % of at least one bioquinone of formula (Ubi)

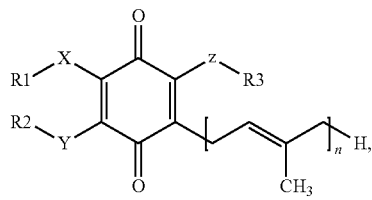

(Ubi)

in which
X, Y, Z mutually independently denote —O— or —NH— or —NR⁴— or a chemical bond,
R¹, R², R³ mutually independently denote a hydrogen atom or an optionally substituted aryl group or an optionally substituted (C1 to C6) alkyl group or a hydroxyalkyl group or a polyhydroxyalkyl group or an optionally substituted ($C_1$ to $C_6$) alkylene group or a ($C_1$ to $C_6$) acyl group, wherein preferred residues are selected mutually independently from —H, —CH₃, —CH₂CH₃, —(CH₂)₂CH₂, —CH (CH₃)₂, —(CH₂)₃CH₃, —CH(CH₃)CH₂CH₃, —CH₂CH (CH₃)₂, —C(CH₃)₃,
R⁴ denotes —CH₃, —CH₂CH₃, —(CH₂)₂CH₂, —CH(CH₃)₂, —(CH₂)₃CH₃, —CH(CH₃)CH₂CH₃, —CH₂CH(CH₃)₂, —C(CH₃)₃,
n denotes values from 1 to 20, preferably from 2 to 15, and in particular 5, 6, 7, 8, 9, 10.

Particularly preferred cosmetic agents according to the present invention are characterized in that they include as a care-providing substance, based on their weight, 0.0001 to 1 wt %, preferably 0.001 to 0.5 wt %, and particularly preferably 0.005 to 0.1 wt % of at least one ubiquinone and/or at least one ubiquinol and/or at least one derivative of said substances, wherein preferred agents include a ubiquinone of formula (Ubi)

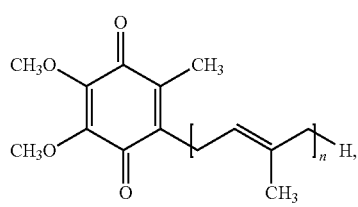

(Ubi)

in which n denotes the values 6, 7, 8, 9, or 10, particularly preferably 10 (Coenzyme Q10).

Alternatively or in addition to the particularly preferred ubiquinones, the agents according to the present invention can also include plastoquinones. Preferred agents according to the present invention are characterized here in that they include 0.0002 to 4 wt %, preferably 0.0005 to 3 wt %, particularly preferably 0.001 to 2 wt %, more preferably 0.0015 to 1, and in particular 0.002 to 0.5 wt % of at least one plastoquinone of formula (Ubi-b)

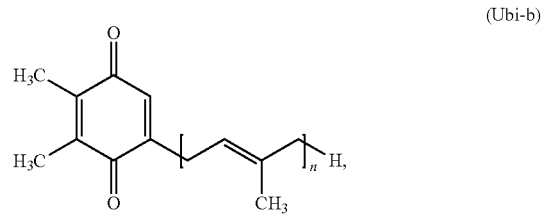

(Ubi-b)

in which n denotes values from 1 to 20, preferably from 2 to 15, and in particular 5, 6, 7, 8, 9, 10, wherein particularly preferred agents include plastoquinone PQ-9.

The agents according to the present invention can include ectoin as a further care enhancer. Ectoin ((4S)-2-methyl-1,4,5,6-tetrahydropyrimidine-4-carboxylic acid) is a natural substance belonging to the group of the compatible solutes. Cosmetic agents preferred according to the present invention are characterized in that they include, based on their weight, 0.001 to 10 wt %, preferably 0.01 to 5 wt %, particularly preferably 0.05 to 2.5 wt %, and in particular 0.1 to 1 wt % (S)-2-methyl-1,4,5,6-tetrahydro-4-pyrimidinecarboxylic acid (ectoin) as well as the physiologically acceptable salts of that compound, and/or (S,S)-5-hydroxy-2-methyl-1,4,5,6-tetrahydro-4-pyrimidinecarboxylic acid (hydroxyectoin) as well as the physiologically acceptable salts of that compound.

Allantoin is a further care-providing substance. In various animal species, principally in mammals, allantoin (5-ureidohydantoin, N-(2,5-dioxo-4-imidazolidinyl)urea) is, alongside uric acid, the end product of the breakdown of nucleic acids, especially of purine bases.

Allantoin is used in cosmetics in hair creams, sunblock agents, shaving lotions, in toothpaste, and in agents to counteract excessive perspiration (hyperhidrosis) and skin irritations. It brings about an acceleration in cell breakdown, cell formation, or cell regeneration, and soothes the skin. Healing of difficult-to-heal injuries is also assisted, although allantoin does not possess any antiseptic properties.

Particularly preferred cosmetic agents according to the present invention include, based on their weight, 0.001 to 10 wt %, preferably 0.01 to 5 wt %, particularly preferably 0.05 to 2.5 wt %, and in particular 0.1 to 1 wt % 5-ureidohydantoin (allantoin).

To improve the elasticity and strengthen the internal structure of hair treated with the agents according to the present invention, the agents according to the present invention can include purine and/or purine derivatives as a care-providing substance. In particular, the result of combining purine and/or purine derivatives with ubiquinones and/or plastoquinones as a care-providing substance is that hair treated with corresponding agents exhibits, inter alia, higher measured values in differential thermal analysis, and improved wet and dry combability values.

Purine (7H-imidazo[4,5-d]pyrimidine) does not occur in isolation in nature, but constitutes the basic member of the purines. Purines in turn are a group of important compounds, widespread in nature and involved in human, animal, plant, and microbial metabolic processes, that derive from the basic member by substitution with OH, $NH_2$, SH in the 2-, 6-, and 8-position, and/or with $CH_3$ in the 1-, 3-, 7 position. Purine can be manufactured, for example, from aminoacetonitrile and formamide. Purines and purine derivatives are often isolated as natural substances, but are also accessible synthetically by numerous routes.

Preferred agents according to the present invention include purine and/or purine derivatives in narrower quantity ranges. Cosmetic agents preferred according to the present invention are characterized here in that they include, based on their weight, 0.001 to 2.5 wt %, preferably 0.0025 to 1 wt %, particularly preferably 0.005 to 0.5 wt %, and in particular 0.01 to 0.1 wt % purine(s) and/or purine derivative(s).

Among purine, the purines, and the purine derivatives, some representatives are particularly preferred according to the present invention. Cosmetic agents preferred according to the present invention are characterized in that they include as a care-providing substance, based on their weight, 0.001 to 2.5 wt %, preferably 0.0025 to 1 wt %, particularly preferably 0.005 to 0.5 wt %, and in particular 0.01 to 0.1 wt % purine(s) and/or purine derivative(s), wherein preferred agents include purine and/or purine derivative(s) of formula (Pur-I)

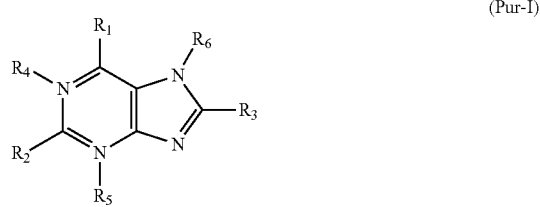

in which the residues $R^1$, $R^2$, and $R^3$ are selected mutually independently from —H, —OH, $NH_2$, —SH, and the residues $R^4$, $R^5$, and $R^6$ are selected mutually independently from —H, —$CH_3$, and —$CH_2$—$CH_3$, the following compounds being preferred:
  purine ($R^1$=$R^2$=$R^3$=$R^4$=$R^5$=$R^6$=H)
  adenine ($R^1$=$NH_2$, $R^2$=$R^3$=$R^4$=$R^5$=$R^6$=H)
  guanine ($R^1$=OH, $R^2$=$NH_2$, $R^3$=$R^4$=$R^5$=$R^6$=H)
  uric acid ($R^1$=$R^2$=$R^3$=OH, $R^4$=$R^5$=$R^6$=H)
  hypoxanthine ($R^1$=OH, $R^2$=$R^3$=$R^4$=$R^5$=$R^6$=H)
  6-purinethiol ($R^1$=SH, $R^2$=$R^3$=$R^4$=$R^5$=$R^6$=H)
  6-thioguanine ($R^1$=SH, $R^2$=$NH_2$, $R^3$=$R^4$=$R^5$=$R^6$=H)
  xanthine ($R^1$=$R^2$=OH, $R^3$=$R^4$=$R^5$=$R^6$=H)
  caffeine ($R^1$=$R^2$=OH, $R^3$=H, $R^4$=$R^5$=$R^6$=$CH_3$)
  theobromine ($R^1$=$R^2$=OH, $R^3$=$R^4$=H, $R^5$=$R^6$=$CH_3$)
  theophylline ($R^1$=$R^2$=OH, $R^3$=H, $R^4$=$CH_3$, $R^5$=$CH_3$, $R^6$=H).

It is further advantageous to use purine or purine derivatives and bioquinones at a specific ratio to one another. Agents according to the present invention in which the weight ratio of purine (derivative(s)) to bioquinone(s) is equal to 10:1 to 1:100, preferably 5:1 to 1:50, particularly preferably 2:1 to 1:20, and in particular 1:1 to 1:10 are preferred in this context.

As already mentioned, caffeine is a particularly preferred purine derivative and Coenzyme Q10 is a particularly preferred bioquinone. Particularly preferred agents according to the present invention are therefore characterized in that they include, based on their weight, 0.001 to 2.5 wt %, preferably 0.0025 to 1 wt %, particularly preferably 0.005 to 0.5 wt %, and in particular 0.01 to 0.1 wt % caffeine, and 0.0002 to 4 wt %, preferably 0.0005 to 3 wt %, particularly preferably 0.001 to 2 wt %, more preferably 0.0015 to 1, and in particular 0.002 to 0.5 wt % Coenzyme Q10.

The agents according to the present invention can also include flavonoids as a care-providing substance. Flavonoids are a group of water-soluble vegetable dyes, and play an important role in the metabolism of many plants. Together with phenolic acids, they belong to the polyphenols. Well over 6,500 different flavonoids are known, and can be subdivided into flavonols, flavones, flavanones, isoflavonoids, and anthocyans.

Flavonoids from all six groups can be used according to the present invention, specific representatives from the individual groups being preferred as a care-providing substance because of their particularly intense effect. Preferred flavonols are quercetin, rutin, camphor oil, myricetin, isorhamnetin, preferred flavonols are catechin, gallocatechin, epicatechin, epigallocatechin gallate, theaflavin, thearubigin, preferred flavones are luteolin, apigenin, morin, preferred flavanones are hesperetin, naringenin, eriodictyol, preferred isoflavonoids are genistein, daidzein, and preferred anthocyanidins (anthocyans) are cyanidin, delphinidin, malvidin, pelargonidin, peonidin, petunidin.

Cosmetic agents particularly preferred according to the present invention are characterized in that they include, based on their weight, 0.001 to 2.5 wt %, preferably 0.0025 to 1 wt %, particularly preferably 0.005 to 0.5 wt %, and in particular 0.01 to 0.1 wt % flavonoids, in particular flavonols, particularly preferably 3,3',4',5,7-pentahydroxyflavone (quercetin) and/or 3,3',4',5,7-pentahydroxyflavone-3-O-rutinoside (rutin).

The use of bisabolol and/or bisabolol oxides as a care-providing agent in the agents according to the present invention is also preferred. Cosmetic agents according to the present invention that additionally include 0.001 to 5 wt %, preferably 0.01 to 4 wt %, particularly preferably 0.02 to 2.5 wt %, and in particular 0.1 to 1.5 wt % bisabolol and/or oxides of bisabolol, preferably (−)-alpha-bisabolol, are preferred here.

Creatine is also suitable according to the present invention as a care-providing substance. Creatine (3-methylguanidinoacetic acid) is an organic acid that, in vertebrates, contributes, inter alia to supplying muscles with energy. Creatine is synthesized in the kidneys, the liver, and the pancreas. It is derived formally from the amino acids glycine and arginine, and 95% of it is present in skeletal muscle.

Particularly preferred cosmetic agents according to the present invention include, based on their weight, 0.01 to 15 wt %, preferably 0.025 to 12.5 wt %, particularly preferably 0.05 to 10 wt %, more preferably 0.1 to 7.5 wt %, and in particular 0.5 to 5 wt % N-methylguanidinoacetic acid (creatine).

The agents according to the present invention can include, in addition to the ingredients recited above and optional further ingredients, further substances that prevent, mitigate, or cure hair loss. A content of hair-root-stabilizing active agents is particularly advantageous. These substances are described below:

Propecia (finasteride) is at present the only preparation that is approved worldwide and for which effectiveness and compatibility have been demonstrated in numerous studies. The effect of Propecia is that less DHT can form from testosterone.

Minoxidil, with or without supplementary additives, is probably the oldest demonstrably effective hair growth agent. For the treatment of hair loss, it must only be used for external application. Hair lotions exist that include 2% to 5% minoxidil, also gels having up to 15% minoxidil. Effectiveness increases with dosage, but minoxidil is soluble in hair lotions only up to a 5% proportion. In many countries hair lotions having minoxidil content of up to 2% are obtainable without a prescription.

To counteract hormonal influences on the hair follicles, spironolactone can be applied for external use in the form of a hair lotion and in combination with minoxidil. Spironolactone acts as an androgen receptor blocker, i.e. the binding of DHT to the hair follicles is prevented.

In summary, cosmetic agents according to the present invention that additionally include, based on its weight, 0.001 to 5 wt % hair-root-stabilizing substances, in particular minoxidil and/or finasteride and/or ketoconazole, are preferred.

The effect of additional anti-dandruff active agents (for example climbazole, piroctone olamine, or zinc pyrithione) is that the quantity of the yeast causing the dandruff is specifically reduced, the microbial flora returns to its normal percentage composition, and flaking is reduced to the natural level. Laboratory tests have demonstrated, however, that the different representatives of Pityrosporum ovale species exhibit different levels of reaction to the anti-dandruff active substances. A combination of anti-dandruff active agents is therefore most effective for maximum counteraction of all dandruff pathogens.

In summary, cosmetic agents according to the present invention that additionally include, based on their weight, 0.001 to 5 wt % anti-dandruff active agents, in particular piroctone olamine (1-hydroxy-4-methyl-6-(2,4,4-trimethylpentyl)pyridin-2(1H)-one, compound with 2-aminoethanol 1:1) and/or zinc pyrithione and/or selenium sulfide and/or climbazole and/or salicylic acid or fumaric acid, are preferred.

In addition to the care-providing substances, the agents according to the present invention can include further care-providing substances. Their presence is not obligatorily necessary in order for the effects according to the present invention to be achieved, but farther-reaching effects, such as a pleasant feel or pleasant application haptics, can result from the use of these care-providing substances.

The agents according to the present invention can, with particular preference, include one or more amino acids as a further ingredient. Amino acids particularly preferably usable according to the present invention derive from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-Cyss), L-carnitine, L-citrulline, L-theanine, 3',4'-dihydroxy-L-phenylalanine (L-DOPA), 5'-hydroxy-L-tryptophan, L-homocysteine, S-methyl-L-methionine, S-allyl-L-cysteine sulfoxide (L-alliin), L-trans-4-hydroxyproline, L-5-oxoproline (L-pyroglutamic acid), L-phosphoserine, creatine, 3-methyl-L-histidine, L-ornithine, wherein both the individual amino acids and mixtures can be used.

Preferred agents according to the present invention include one or more amino acids in narrower quantity ranges. Cosmetic agents preferred according to the present invention are characterized here in that they include as a care-providing substance, based on their weight, 0.01 to 5 wt %, preferably 0.02 to 2.5 wt %, particularly preferably 0.05 to 1.5 wt %, more preferably 0.075 to 1 wt %, and in particular 0.1 to 0.25 wt % amino acid(s), preferably from the group of glycine and/or alanine and/or valine and/or lysine and/or leucine and/or threonine.

As a further constituent, the agents according to the present invention can include at least one carbohydrate from the group of monosaccharides, disaccharides, and/or oligosaccharides. Cosmetic agents preferred according to the present invention are characterized here in that they include as a care-providing substance, based on their weight, 0.01 to 5 wt %, preferably 0.05 to 4.5 wt %, particularly preferably 0.1 to 4 wt %, more preferably 0.5 to 3.5 wt %, and in particular 0.75 to 2.5 wt % carbohydrate(s) selected from monosaccharides, disaccharides, and/or oligosaccharides, wherein preferred carbohydrates are selected from monosaccharides, in particular D-ribose and/or D-xylose and/or L-arabinose and/or D-glucose and/or D-mannose and/or D-galactose and/or D-fructose and/or sorbose and/or L-fucose and/or L-rhamnose, disaccharides, in particular sucrose and/or maltose and/or lactose and/or trehalose and/or cellobiose and/or gentobiose and/or isomaltose.

Particularly preferred agents according to the present invention include, based on their weight,
 0.005 to 0.015 wt % caffeine and 0.75 to 1.5 wt % glucose monohydrate,
 0.005 to 0.015 wt % caffeine and 0.75 to 1.5 wt % sucrose,
 0.005 to 0.015 wt % caffeine and 0.75 to 1.5 wt % fructose.

As already mentioned, preferred agents according to the present invention include (an) amino acids(s).

Amino acids particularly preferably usable according to the present invention derive from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, (3-alanine, 4-aminobutyric acid (GABA), betaine, L-cystine (L-cyss), L-carnitine, L-citrulline, L-theanine, 3',4'-dihydroxy-L-phenylalanine (L-DOPA), 5'-hydroxy-L-tryptophan, L-homocysteine, S-methyl-L-methionine, S-allyl-L-cysteine sulfoxide (L-alliin), L-trans-4-hydroxyproline, L-5-oxoproline (L-pyroglutamic acid), L-phosphoserine, creatine, 3-methyl-L-histidine, L-ornithine, wherein both the individual amino acids and mixtures can be used.

Preferred agents according to the present invention include one or more amino acids in narrower quantity ranges. Cosmetic agents preferred according to the present invention are characterized here in that they additionally include 0.05 to 5 wt %, preferably 0.1 to 2.5 wt %, particularly preferably 0.15 to 1 wt %, and in particular 0.2 to 0.5 wt % amino acid(s), preferably (an) amino acid(s) from the group of glycine and/or alanine and/or valine and/or lysine and/or leucine and/or threonine.

Particularly preferred agents according to the present invention include, based on their weight,
 0.005 to 0.015 wt % caffeine and 0.75 to 1.5 wt % glucose monohydrate and 0.1 to 0.25 wt % glycine,
 0.005 to 0.015 wt % caffeine and 0.75 to 1.5 wt % sucrose and 0.1 to 0.25 wt % glycine,
 0.005 to 0.015 wt % caffeine and 0.75 to 1.5 wt % fructose and 0.1 to 0.25 wt % glycine,
 0.005 to 0.015 wt % caffeine and 0.75 to 1.5 wt % glucose monohydrate and 0.1 to 0.25 wt % alanine,
 0.005 to 0.015 wt % caffeine and 0.75 to 1.5 wt % sucrose and 0.1 to 0.25 wt % alanine,
 0.005 to 0.015 wt % caffeine and 0.75 to 1.5 wt % fructose and 0.1 to 0.25 wt % alanine,
 0.005 to 0.015 wt % caffeine and 0.75 to 1.5 wt % glucose monohydrate and 0.1 to 0.25 wt % valine,
 0.005 to 0.015 wt % caffeine and 0.75 to 1.5 wt % sucrose and 0.1 to 0.25 wt % valine, 0.005 to 0.015 wt % caffeine and 0.75 to 1.5 wt % fructose and 0.1 to 0.25 wt % valine.

The agents according to the present invention can include as a further ingredient at least one proteolipid of formula (P-I)

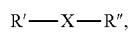

(P-I)

in which
R' denotes a straight-chain or branched, saturated or unsaturated hydrocarbon residue having 11 to 24 carbon atoms,
R" signifies a protein, a peptide, or a protein hydrolysate,
X denotes —C(O)O— or —N$^+$(R$^{III}_2$)R$^{IV}$- or —N(R$^{III}$)R$^{IV}$— or —C(O)—N(R$^V$)R$^{VI}$—,
R$^{III}$ signifies —(CH$_2$)$_x$—CH$_3$ where x=0 to 22, and
R$^{IV}$ signifies —CH$_2$—CH(OH)—CH$_2$— or —(CH$_2$)$_x$— where x=0 to 22;
R$^V$ and R$^{VI}$ mutually independently denote —H or —(CH$_2$)$_x$—CH$_3$ where x=0 to 22, with the provision that R" denotes keratin or a keratin hydrolysate when X denotes C—(O)O—.

Proteolipids are preferably used within specific quantities in the agents according to the present invention. Preferred cosmetic agents according to the present invention include, based on their weight, 0.01 to 10 wt %, preferably 0.02 to 5 wt %, particularly preferably 0.05 to 2.5 wt %, more preferably 0.1 to 1 wt %, and in particular 0.15 to 0.5 wt % proteolipid(s).

The residue R" in formula (P—I) denotes a peptide or a protein or a protein hydrolysate. When X═══C(O)O—, R" is selected from the group of keratin or keratin hydrolysate.

Preferred residues R" are oligopeptides that comprise at least one amino acid sequence Glu-Glu-Glu, wherein the amino group can be present in free or protonated form, and the carboxy groups can be present in free or deprotonated form.

In this as in all subsequent formulas, the bracketed hydrogen atom of the amino group, like the bracketed hydroxy group of the acid function, signifies that the relevant groups can be present as such (this then refers to an oligopeptides having the relevant number of amino acids, as depicted in formula 3 above), or that the amino acid sequence is present in an oligopeptide that also comprises further amino acids; depending on where the further amino acid(s) is/are bound, the bracketed constituents of the aforementioned formulas are replaced by the further amino acid residue(s).

"Oligopeptides" for purposes of the present Application are condensation products, linked in acid-amide fashion by peptide bonds, of amino acids, which comprise at least 3 and at most 25 amino acids.

In hair treatment agents preferred according to the present invention of the embodiment described above, the oligopeptide (=residue R") comprises 5 to 15 amino acids, preferably 6 to 13 amino acids, particularly preferably 7 to 12 amino acids, and in particular 8, 9, or 10 amino acids.

The molar mass of the proteolipid included in the agents according to the present invention can vary depending on whether further amino acids are bound to the Glu-Glu-Glu sequence and on the nature of those amino acids, and as a function of the selection of the residues R' and optionally R$^{III}$ and R$^{IV}$. Cosmetic agents preferred according to the present invention are characterized in that the proteolipid has a molar mass from 1000 to 30,000 Da, preferably from 1250 to 25,000 Da, particularly preferably from 1500 to 20,000 Da, and in particular from 2000 to 15,000 Da.

It is preferred to select as the residue R" oligopeptides that are not made up only of the three glutamic acids, but comprise further amino acids bound to that sequence. These further amino acids are preferably selected from specific amino acids, while specific other representatives are less preferred according to the present invention.

It is thus preferred if the residue R" of the proteolipids employed in the agents according to the present invention includes no methionine. It is further preferred if the residue R" of the proteolipids employed in the agents according to the present invention includes no cysteine and/or cystine.

It is further preferred if the residue R" of the proteolipids employed in the agents according to the present invention includes no aspartic acid and/or asparagine. It is further preferred if the residue R" of the proteolipids employed in the agents according to the present invention includes no serine and/or threonine Conversely, it is preferred if the residue R" of the proteolipids employed in the agents according to the present invention includes tyrosine. It is further preferred if the residue R" of the proteolipids employed in the agents according to the present invention includes leucine. It is further preferred if the residue R" of the proteolipids employed in the agents according to the present invention includes isoleucine. It is further preferred if the residue R" of the proteolipids employed in the agents according to the present invention includes arginine. It is further preferred if the residue R" of the proteolipids employed in the agents according to the present invention includes valine.

Oligopeptides particularly preferred as residue R", or amino acid sequences included in the preferred oligopeptides, are described below:

A particularly preferred oligopeptide additionally includes tyrosine, which is bound preferably via its acid function to the Glu-Glu-Glu sequence. Cosmetic agents preferred according to the present invention are therefore characterized in that the oligopeptide included as residue R" in the proteolipids of formula (I) comprises at least one Tyr-Glu-Glu-Glu amino acid sequence, wherein the amino group can be present in free or protonated form, and the carboxy groups can be present in free or deprotonated form.

A further particularly preferred oligopeptide additionally includes isoleucine, which is bound preferably via its amino function to the Glu-Glu-Glu sequence. Cosmetic agents preferred according to the present invention are therefore characterized in that the oligopeptide included as residue R" in the proteolipids of formula (I) comprises at least one Glu-Glu-Glu-Ile amino acid sequence, wherein the amino group can be present in free or protonated form, and the carboxy groups can be present in free or deprotonated form.

Oligopeptides that comprise the two aforesaid amino acids (tyrosine and isoleucine) are preferred according to the present invention. Particularly preferred in this context are hair treatment agents according to the present invention in which the oligopeptide included as residue R" in the proteolipids of formula (I) comprises at least one Tyr-Glu-Glu-Glu-Ile amino acid sequence, wherein the amino group can be present in free or protonated form, and the carboxy groups can be present in free or deprotonated form.

Further preferred oligopeptides additionally include arginine that is preferably present bound to isoleucine. Cosmetic agents preferred according to the present invention are therefore characterized in that the oligopeptide included as residue R" in the proteolipids of formula (I) comprises at least one Tyr-Glu-Glu-Glu-Ile-Arg amino acid sequence, wherein the amino groups can be present in free or protonated form, and the carboxy groups can be present in free or deprotonated form.

Even further preferred oligopeptides additionally include valine that is preferably present bound to arginine. Cosmetic agents further preferred according to the present invention are therefore characterized in that the oligopeptide included as residue R" in the proteolipids of formula (I) comprises at least one Tyr-Glu-Glu-Glu-Ile-Arg-Val amino acid sequence, wherein the amino groups can be present in free or protonated form, and the carboxy groups can be present in free or deprotonated form.

Even further preferred oligopeptides additionally include leucine that is preferably present bound to valine. Cosmetic agents further preferred according to the present invention are characterized in that the oligopeptide included as residue R" in the proteolipids of formula (I) comprises at least one Tyr-Glu-Glu-Glu-Ile-Arg-Val-Leu amino acid sequence, wherein the amino groups can be present in free or protonated form, and the carboxy groups can be present in free or deprotonated form.

Particularly preferred oligopeptides additionally include leucine that is preferably present bound to tyrosine. Cosmetic agents further preferred according to the present invention are characterized in that the oligopeptide included as residue R" in the proteolipids of formula (I) comprises at least one Leu-Tyr-Glu-Glu-Glu-Ile-Arg-Val-Leu amino acid sequence, wherein the amino groups can be present in free or protonated form, and the carboxy groups can be present in free or deprotonated form.

In summary, cosmetic agents according to the present invention that include at least one proteolipid of formula (I) in which R" comprises at least one Leu-Tyr-Glu-Glu-Glu-Ile-Arg-Val-Leu amino acid sequence, wherein the amino groups can be present in free or protonated form, and the carboxy groups can be present in free or deprotonated form, are particularly preferred.

As already mentioned, R" is selected from the group of keratin or keratin hydrolysate when X=C(O)O—.

In all other cases, the residue R" in formula (P-I) can denote a peptide or a protein or a protein hydrolysate, wherein protein hydrolysates are preferred. Protein hydrolysates are product mixtures that are obtained by the acid-, base-, or enzyme-catalyzed breakdown of proteins. Protein hydrolysates of both vegetable and animal origin can be used according to the present invention.

Animal protein hydrolysates are, for example, protein hydrolysates of elastin, collagen, keratin, silk, and milk protein, which can also be present in the form of salts. Such products are marketed, for example, under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), and Kerasol® (Croda).

It is preferred according to the present invention to use protein hydrolysates of vegetable origin, for example soy, almond, rice, pea, potato, and wheat protein hydrolysates. Such products are obtainable, for example, under the trademarks Gluadin® (Cognis), DiaMin® (Diamalt), Lexein® (Inolex), and Crotein® (Croda).

The residue R" is preferably selected from keratin or keratin hydrolysates regardless of the selection of X in formula (P-I). Preferred cosmetic agents according to the present invention are characterized in that they include at least one proteolipid of formula (P-I) in which R" denotes keratin or a keratin hydrolysate.

Cosmetic agents according to the present invention that include at least one proteolipid of formula (P-I) in which $R^{III}$ signifies —$CH_3$ and $R^{IV}$ denotes —$(CH_2)_x$, where x=0, 1, 2, 3, 4, 5, 6, 7, 8, are particularly preferred.

Particularly preferred cosmetic agents according to the present invention are further characterized in that they include at least one proteolipid of formula (I) in which X denotes —$N^+(CH_3)_2$—$CH_2$—CH(OH)—$CH_2$, and R' denotes —$(CH_2)_{17}$—$CH_3$.

Further preferred cosmetic agents according to the present invention are likewise characterized in that they include at least one proteolipid of formula (P-I) in which X denotes —C(O)O— and R' denotes —$(CH_2)_{17}$—$CH_3$.

It has proven to be advantageous to use, in addition to the proteolipids, protein hydrolysates. The latter intensify the action of the proteolipids and are in turn intensified in terms of their effects. Protein hydrolysates as residue R" have been described in detail above. In summary, cosmetic agents according to the present invention that additionally include, based on their weight, 0.01 to 10 wt %, preferably 0.05 to 7 wt %, particularly preferably 0.1 to 5 wt %, more preferably 0.25 to 2.5 wt %, and in particular 0.5 to 2.0 wt % protein hydrolysate(s), preferably keratin hydrolysate(s), are preferred.

For aesthetic reasons, "clear" products are often preferred by consumers. Cosmetic agents preferred according to the present invention are therefore characterized in that they are transparent or translucent.

"Transparent or translucent" is understood in the context of the present invention as a composition that has an NTU value below 100. The NTU value (nephelometric turbidity unit) is a unit used in water treatment for turbidity measurements in liquids. It is the unit of the turbidity of a liquid, measured with a calibrated nephelometer.

In a preferred embodiment of the invention, an agent according to the present invention can furthermore also include UV filters (I). The UV filters to be used according to the present invention are not subject to any general restrictions in terms of their structure and their physical properties. Instead, all UV filters usable in the cosmetics sector, whose absorption maximum lies in the UVA (315 to 400 nm), UVB (280 to 315 nm), or UVC (<280 nm) regions, are suitable. UV filters having an absorption maximum in the UVB region, in particular in the region from approximately 280 to approximately 300 nm, are particularly preferred.

The UV filters used according to the present invention can be selected, for example, from substituted benzophenones, p-aminobenzoic acid esters, diphenylacrylic acid esters, cinnamic acid esters, salicylic acid esters, benzimidazoles, and o-aminobenzoic acid esters.

The UV filters (I) are included in the agents according to the present invention usually in quantities from 0.1 to 5 wt % based on the entire agent. Quantities from 0.4 to 2.5 wt % are preferred.

The agents according to the present invention can furthermore include a 2-pyrrolidone-5-carboxylic acid and derivatives thereof (J). The sodium, potassium, calcium, magnesium, or ammonium salts, in which the ammonium ion carries one to three $C_1$ to $C_4$ alkyl groups in addition to hydrogen, are preferred. The sodium salt is very particularly preferred. The quantities used in the agents according to the present invention are preferably 0.05 to 10 wt % based on the entire agent, particularly preferably 0.1 to 5, and in particular 0.1 to 3 wt %.

It can additionally prove to be advantageous if penetration adjuvants and/or swelling agents (M) are included in the agents according to the present invention. To be included there among are, for example, urea and urea derivatives, guanidine and derivatives thereof, arginine and derivatives thereof, water glass, imidazole and derivatives thereof, histidine and derivatives thereof, benzyl alcohol, glycerol, glycol and glycol ethers, propylene glycol and propylene glycol ethers, for example propylene glycol monoethyl ether, carbonates, hydrogen carbonates, diols and triols and in particular 1,2-diols and 1,3-diols such as 1,2-propanediol, 1,2-pentanediol, 1,2-hexanediol, 1,2-dodecanediol, 1,3-propanediol, 1,6-hexanediol, 1,5-pentanediol, 1,4-butanediol.

In addition, for purposes of the invention short-chain carboxylic acids (N) can advantageously additionally assist the active agent complex (A). "Short-chain carboxylic acids" and derivatives thereof are understood for purposes of the invention as carboxylic acids that can be saturated or unsaturated and/or straight-chain or branched or cyclic and/or aromatic and/or heterocylic, and have a molecular weight of less than 750. Saturated or unsaturated straight-chain or branched carboxylic acids having a chain length from 1 to 16 carbon atoms in the chain can be preferred for purposes of the invention; those having a chain length from 1 to 12 carbon atoms in the chain are very particularly preferred.

The short-chain carboxylic acids for purposes of the invention can comprise one, two, three, or more carboxy groups. Carboxylic acids having multiple carboxy groups, in particular di- and tricarboxylic acids, are preferred for purposes of the invention. The carboxy groups can be present entirely or partly as an ester, acid anhydride, lactone, amide, imidic acid, lactam, lactim, dicarboximide, carbohydrazide, hydrazone, hydroxam, hydroxime, amidine, amidoxime, nitrile, phosphonic ester, or phosphate ester. The carboxylic acids used according to the present invention can of course be substituted along the carbon chain or along the ring structure. To be included among the substituents of the carboxylic acids used according to the present invention are, for example, C1 to C8 alkyl, C2 to C8 alkenyl, aryl, aralkyl, and aralkenyl, hydroxymethyl, C2 to C8 hydroxyalkyl, C2 to C8 hydroxyalkenyl, aminomethyl, C2 to C8 aminoalkyl, cyano, formyl, oxo, thioxo, hydroxy, mercapto, amino, carboxy, or imino groups. Preferred substituents are C1 to C8 alkyl, hydroxymethyl, hydroxy, amino, and carboxy groups. Substituents in the alpha-position are particularly preferred. Very particularly preferred substituents are hydroxy, alkoxy, and amino groups, wherein the amino function can optionally be further substituted with alkyl, aryl, aralkyl, and/or alkenyl residues. In addition, the phosphonic esters and phosphate esters are likewise preferred carboxylic acid derivatives.

In a further preferred embodiment the agents according to the present invention can include emulsifier agents (F).

A further subject of the present invention is a method for treating keratinic fibers, in which method a hair treatment agent according to the present invention is applied onto the keratinic fibers and is rinsed out again after a contact time from a few seconds to as much as 45 minutes.

The statements made regarding the agents according to the present invention apply mutatis mutandis with reference to preferred embodiments of the method according to the present invention.

A further subject of the present invention is the use of hair treatment agents according to the present invention
   to condition keratinic substances, and/or
   to improve the looseness, softness, shine, and/or combability and facilitate the styling of keratinic substances, and/or
   to improve retention of the conditioning effect in the context of hair washing, and/or
   to improve wet and dry combability, and/or
   to improve shine, and/or
   to improve the moisture budget of keratinic fibers, and/or
   to protect the keratinic fibers from oxidative damage, and/or
   to prevent grease re-absorption by keratinic fibers, and/or
   to enhance the washing fastness of colored keratinic fibers.

The statements made regarding the agents according to the present invention also apply mutatis mutandis with reference to preferred embodiments of the uses according to the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic composition including, in a cosmetically acceptable medium, at least one conditioning agent and at least one 4-morpholinomethyl-substituted silicone of formula (V)

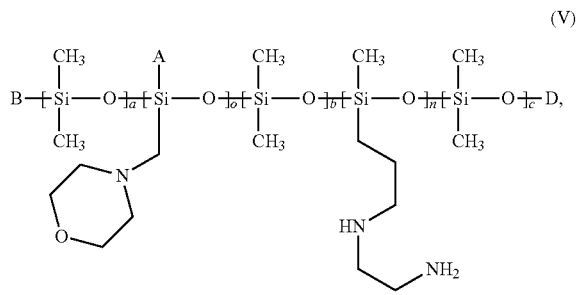

in which

A denotes a structural unit (I), (II), or (III) bound via —O—

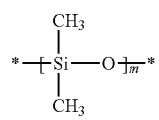

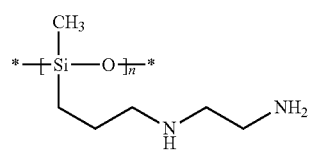

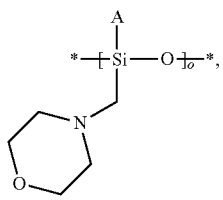

or an oligomeric or polymeric residue bound via —O— containing structural units of formulas (I), (II), or (III), or half of an oxygen atom connecting to a structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers between 0 and 1000, with the provision that a+b+c>0, m, n, and o denote integers between 1 and 1000.

2. The cosmetic composition according to claim 1, wherein the at least one 4-morpholinomethyl-substituted silicone is characterized such that $m>(n+o)$ or $(a+b+c)>(n+o)$.

3. The cosmetic composition according to claim 1, wherein the composition includes, based on its weight, 0.00001 to 10 wt % of the at least one 4-morpholinomethyl-substituted silicone(s).

4. The cosmetic composition according to claim 1, further comprising, based on its weight, 0.00001 to 5 wt % of a nonionic compound selected from the group consisting of branched ethoxylated tridecanol (INCI name: Trideceth-5), α-isotridecyl-ω-hydroxypolyglycol ether (INCI name: Trideceth-10), and mixtures thereof.

5. The cosmetic composition according to claim 1, wherein the composition includes hydroxy-terminated 4-morpholinomethyl-substituted silicone(s) in which the molar ratio of hydroxy to alkoxy is in the range from 0.2:1 to 0.4:1.

6. The cosmetic composition according to claim 1, wherein the weight-average molar mass of the at least one 4-morpholinomethyl-substituted silicone of formula (V) is in the range from 2000 to 1,000,000 gmol$^{-1}$.

7. The cosmetic composition according to claim 1, wherein the at least one 4-morpholinomethyl-substituted silicone of formula (V) is present in the form of an oil-in-water emulsion in which the number-average size of the silicone particles in the emulsion is in the range from 3 to 500 nm.

8. The cosmetic composition according to claim 1, wherein the conditioning agents are selected from the group consisting of synthetic oils, mineral oils, vegetable oils, fluorinated or perfluorinated oils, natural or synthetic waxes, compounds of the ceramide type, carboxylic acid esters, silicones different from the silicones of formula (V), anionic polymers, nonionic polymers, cationic polymers, amphoteric polymers, cationic proteins, cationic protein hydrolysates, cationic surface-active substances, and mixtures thereof.

9. The cosmetic composition according to claim 8, wherein the carboxylic acid esters are selected from the group consisting of ethyl palmitate, isopropyl palmitate, 2-ethylhexyl palmitate, 2-octyldecyl palmitate, alkyl myristates, hexyl stearate, butyl stearate, isobutyl stearate; dioctyl malate, hexyl laurate, 2-hexyldecyl laurate, isononyl isononanoate, and cetyl octanoate.

10. The cosmetic composition according to claim 1, further comprising at least one additional ingredient selected from the group consisting of
(a) polyalkylsiloxanes selected from the group consisting of:
polydimethylsiloxanes having terminal trimethylsilyl groups;
polydimethylsiloxanes having terminal dimethylsilanol groups; and
polyalkyl (C$_{1-20}$) siloxanes;
(b) polyarylsiloxanes selected from the group consisting of:
polydimethylmethylphenylsiloxanes, and polydimethyldiphenylsiloxanes that are present in straight-chain and/or branched fashion and have at 25° C. a viscosity in the range from $1·10^{-5}$ to $5·10^{-2}$ m$^2$/s;
(c) silicone rubbers selected from the group consisting of polydiorganosiloxanes that have number-average molar masses in the range from 200,000 to 1,000,000 and that are used as such or in a mixture with a solvent;
(d) resins selected from the group consisting of resins that are constructed from the units R$_3$SiO$_{1/2}$, R$_2$SiO$_{2/2}$, RSiO$_{3/2}$, and SiO$_{4/2}$, in which the group R signifies a hydrocarbon group having 1 to 16 carbon atoms or a phenyl group; and
(e) organomodified silicones selected from the group consisting of silicones that carry in their structure one or more organofunctional groups which are bound via a hydrocarbon group.

11. The cosmetic composition according to claim 10, wherein the composition includes one or more of the polyalkylsiloxanes, used individually or in a mixture, selected from the group consisting of the following structures:
polydimethylsiloxane,
polydimethylsiloxane/methylvinylsiloxanes,
polydimethylsiloxane/diphenylsiloxane,
polydimethylsiloxane/phenylmethylsiloxane,
polydimethylsiloxane/diphenylsiloxane/methylvinylsiloxane, and the following mixtures:
mixtures that are constituted from a polydimethylsiloxane hydroxylated at the chain end and a cyclic polydimethylsiloxane,
mixtures that are constituted from a polydimethylsiloxane rubber and a cyclic silicone, and
mixtures of polydimethylsiloxanes of different viscosities.

12. The cosmetic composition according to claim 8, wherein the anionic polymer is included and selected from the group consisting of
polymers that comprise carboxy units which are derived from mono- or dicarboxylic acid monomers of the following formula:

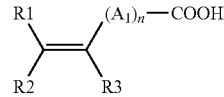

in which n signifies 0 or an integer from 1 to 10, A$_1$ is a methylene group that is bound as applicable via a heteroatom to the carbon atom of the unsaturated group or, if n is greater than 1, to the adjacent methylene group, R$_1$ signifies a hydrogen atom, phenyl, or benzyl, R$_2$ is a hydrogen atom, a lower alkyl group, or carboxy, and R$_3$ signifies a hydrogen atom, a lower alkyl group, a group —CH$_2$COOH, phenyl, or benzyl; and polymers that comprise units which are derived from a sulfonic acid.

13. The cosmetic composition according to claim 12, characterized in that the anionic polymer is selected from among:
copolymers of acrylic acid;
copolymers derived from crotonic acid;
polymers that are derived from maleic acid or maleic acid anhydride, fumaric acid or itaconic acid, and vinyl esters, vinyl ethers, vinyl halides, phenylvinyl derivatives, acrylic acid and esters thereof;
copolymers of methacrylic acid and methyl methacrylate;
a copolymer of methacrylic acid and ethyl acrylate;
a vinyl acetate/crotonic acid copolymer; and
a vinyl acetate/crotonic acid/polyethylene glycol terpolymers.

14. The cosmetic composition according to claim 8, characterized in that the cationic surface-active substances are included and are selected from the group consisting of:
quaternary ammonium salts of the following general formula (XXIII):

$$\begin{array}{c} R_1 \quad R_3 \\ \diagdown \diagup \\ N^+ \quad X^- \\ \diagup \diagdown \\ R_2 \quad R_4 \end{array} \quad \text{(XXIII)}$$

in which X is an anion that is selected from among halides, alkyl (C$_{2-6}$) sulfates, phosphates, alkyl- or alkylarylsulfonates, and anions derived from an organic acid, and
the groups R$_1$ to R$_3$, which can be identical or different, signify a straight-chain or branched aliphatic group having 1 to 4 carbon atoms or an aromatic group, wherein the aliphatic groups can include heteroatoms; the group R$_4$ is a straight-chain or branched alkyl group having 16 to 30 carbon atoms;
the groups R$_1$ and R$_2$, which can be identical or different, signify a straight-chain or branched aliphatic group having 1 to 4 carbon atoms or an aromatic group, wherein the aliphatic groups can include heteroatoms;
the groups R$_3$ and R$_4$, which can be identical or different, signify a straight-chain or branched alkyl group having 12 to 30 carbon atoms, wherein the group comprises at least one ester function or amide function;
quaternary ammonium salts of imidazolinium;
quaternary diammonium salts of formula (XXV):

$$\begin{array}{c} R_9 \quad R_{10} \quad R_{12} \quad R_{13} \\ \diagdown \diagup \quad \quad \diagdown \diagup \\ N^+ \quad\quad\quad\quad N^+ \\ \diagup \diagdown \quad \quad \diagup \diagdown \\ R_{11} \quad\quad 2\,X^- \quad\quad R_{14} \end{array} \quad \text{(XXV)}$$

in which the group R$_9$ signifies an aliphatic group having approximately 16 to 30 carbon atoms, the groups R$_{10}$, R$_{11}$, R$_{12}$, R$_{13}$, and R$_{14}$, which can be identical or different, are selected from among hydrogen or an alkyl group having 1 to 4 carbon atoms, and X is an anion that is selected from among halides, acetates, phosphates, nitrates, and methyl sulfates; and quaternary ammonium salts that include at least one ester function of the following formula (XXVI):

$$\text{R}_{17}\overset{O}{\underset{}{\|}}\text{—}(OC_nH_{2n})_y\text{—}\overset{X^-}{\underset{R_{15}}{\overset{(C_rH_{2r}O)_z}{\underset{|}{N^+}}}}\text{—}(C_pH_{2p}O)_x\,R_{16} \quad \text{(XXVI)}$$

in the formula:
R$_{15}$ is selected from among C$_{1-6}$ alkyl groups and hydroxyalkyl or dihydroxyalkyl groups having 1 to 6 carbon atoms;
R$_{16}$ is selected from among:
a group R19-C(O)—
hydrocarbon-based groups R$_{20}$ having 1 to 22 carbon atoms, which can be straight-chain or branched, saturated or unsaturated,
a hydrogen atom,
R$_{18}$ is selected from among:
a group R21-C(O)—
hydrocarbon-based groups R$_{22}$ having 1 to 6 carbon atoms, which can be straight-chain or branched, saturated or unsaturated,
a hydrogen atom,
R$_{17}$, R$_{19}$, and R$_{21}$, which can be identical or different from one another, are selected from among straight-chain or branched, saturated or unsaturated C$_{7-21}$ hydrocarbon groups;
n, p, and r, which can be identical or different, are integers from 2 to 6;
y is an integer in the range from 1 to 10;
x and z, which can be identical or different, signify 0 or an integer from 1 to 10;
X$^-$ is a simple or complex, organic or inorganic anion;
with the provision that the sum x+y+z is in the range from 1 to 15, that R$_{16}$ signifies R$_{20}$ when x is 0, and that R$_{18}$ signifies R$_{22}$ when z is 0.

15. The cosmetic composition according to claim 1, wherein the conditioning agent or agents is/are included in a total quantity from 0.001 to 20 wt % based on the total weight of the composition.

16. A method for treating keratinic fibers, comprising:
applying a hair treatment agent in accordance with claim 1 onto the keratinic fibers and
rinsing the hair treatment agent out again after a contact time from a few seconds to as much as 45 minutes.

* * * * *